(12) United States Patent
Reiter et al.

(10) Patent No.: US 8,703,920 B2
(45) Date of Patent: Apr. 22, 2014

(54) FULLY HUMAN ANTIBODIES AGAINST N-CADHERIN

(75) Inventors: Robert E. Reiter, Los Angeles, CA (US); Eric Lepin, Los Angeles, CA (US); Anna M. Wu, Sherman Oaks, CA (US)

(73) Assignee: The Regents of the University of California, Oakland, CA (US)

( * ) Notice: Subject to any disclaimer, the term of this patent is extended or adjusted under 35 U.S.C. 154(b) by 851 days.

(21) Appl. No.: 12/590,601

(22) Filed: Nov. 9, 2009

(65) Prior Publication Data
US 2010/0233170 A1  Sep. 16, 2010

Related U.S. Application Data

(60) Provisional application No. 61/113,042, filed on Nov. 10, 2008.

(51) Int. Cl.
| | |
|---|---|
| C07K 14/00 | (2006.01) |
| C07K 16/00 | (2006.01) |
| C07K 17/00 | (2006.01) |
| A61K 35/14 | (2006.01) |
| A61K 38/16 | (2006.01) |
| A61K 39/395 | (2006.01) |
| A61K 39/00 | (2006.01) |
| C12P 21/08 | (2006.01) |

(52) U.S. Cl.
USPC ........ 530/387.3; 530/350; 530/380; 530/386; 530/387.7; 530/388.1; 424/130.1; 424/133.1; 424/135.1; 424/138.1

(58) Field of Classification Search
CPC .... C07K 61/28; C07K 16/2896; C07K 16/32; C07K 2317/569; C07K 2317/622; C07K 2317/626
USPC ........ 530/350, 380, 386, 387.3, 387.7, 388.1, 530/388.2; 424/130.1, 133.1, 135.1, 138.1, 424/142.1, 144.1
See application file for complete search history.

(56) References Cited

U.S. PATENT DOCUMENTS

| | | | |
|---|---|---|---|
| 5,750,078 | A | 5/1998 | Shitara et al. |
| 5,889,157 | A | 3/1999 | Pastan et al. |
| 6,472,368 | B1 | 10/2002 | Doherty et al. |
| 6,682,901 | B2 | 1/2004 | Blaschuk et al. |
| 7,973,139 | B2 * | 7/2011 | Bell et al. ............ 530/387.9 |
| 2002/0146687 | A1 | 10/2002 | Blaschuk et al. |
| 2003/0190602 | A1 | 10/2003 | Pressman et al. |
| 2004/0248219 | A1 | 12/2004 | Blaschuk et al. |
| 2007/0105133 | A1 | 5/2007 | Clarke et al. |
| 2010/0119527 | A1 | 5/2010 | Reiter |
| 2010/0233170 | A1 | 9/2010 | Reiter et al. |
| 2010/0278821 | A1 | 11/2010 | Reiter |
| 2011/0086029 | A1 | 4/2011 | Reiter et al. |
| 2011/0142838 | A1 | 6/2011 | Reiter et al. |

FOREIGN PATENT DOCUMENTS

| | | |
|---|---|---|
| JP | 2002-513937 | 5/2002 |
| WO | WO 99/57565 A2 | 11/1999 |
| WO | WO 01/62206 A2 | 8/2001 |
| WO | WO 01/62206 A3 | 8/2001 |
| WO | WO 2004/106380 A2 * | 12/2004 |
| WO | WO 2007/109347 A2 | 9/2007 |
| WO | WO 2007/109347 A3 | 9/2007 |
| WO | WO 2009/124281 A2 | 10/2009 |
| WO | 2010/054377 A2 | 5/2010 |
| WO | 2010/054397 A2 | 5/2010 |

OTHER PUBLICATIONS

Adherex.com, "Adherex Presents Final Clinical Data on ADH-1 Phase 1 Trial at ASCO Annual Meeting," located at <http://www.adherex.com/news/news_items/2005-05-16>, last accessed on Jun. 27, 2010, 2 pages.

Beckman, R.A. et al., "Antibody Construct in Cancer Therapy, Protein Engineering Strategies to Improve Exposure in Solid Tumors," Can., 2007, vol. 109, pp. 170-179.

Blaschuk et al., "Identification of a Cadherin Cell Adhesion Recognition Sequence," Developmental Biology, 1990, vol. 139, No. 1, pp. 227-229.

Buesa, C. et al., "DNA chip technology in brain banks: confronting a degrading world," J. Neuropathol. Exp. Neurol., 2004, vol. 63, No. 10, pp. 1003-1014, Abstract.

Bussemakers, M.J.G. et al., "The role of OB-cadherin in human prostate cancer," Proceedings of the Annual Meeting of the American Association for Cancer Research, New York, NY, Mar. 1, 1998, vol. 39, Abstract No. 3405, 1 page.

Céspedes, M. V. et al., "Mouse models in oncogenesis and cancer therapy," Clin. Transls. Oncol., 2006, vol. 8, No. 5, pp. 318-329.

Dennis, C., "Off by a whisker," Nature, 2006, vol. 442, pp. 739-741.

Fujimori, K. et al., "A Modeling Analysis of Monoclonal Antibody Percolation Through Tumors: A Binding-Site Barrier," J. Nuc. Med., 1990, vol. 31, pp. 1191-1198.

Hatta et al., "Cloning and Expression of cDNA Encoding a Neural Calcium-dependent Cell Adhesion Molecule: Its Identity in the Cadherin Gene Family," The Journal of Cell Biology, 1988, vol. 106, No. 3, pp. 873-881.

Jaggi, M. et al., "N-Cadherin Switching Occurs in High Gleason Grade Prostate Cancer," The Prostate, 2006, vol. 66, pp. 193-199.

Meyer, S. et al., "Messenger RNA Turnover in Eukaryotes: Pathways and Enzymes," Clin. Rev. Biochem. & Molec. Biol., 2004, vol. 39, pp. 197-216.

Mialhe, A. et al., "Expression of E-. P-, n-cadherins and Catenins in Human Bladder Carcinoma Cell Lines," J. Urol., Sep. 2000, vol. 164 (3 Pt 1), pp. 826-835, Abstract Only.

Price, J.T. et al., "Mechanisms of Tumor Invasion and Metastasis: Emerging Targets for Therapy," Expert Opin. Ther. Targets, 2002, vol. 6, No. 2, pp. 217-233.

Rieger-Christ, Kimberly M. et al., "Novel expression of N-cadherin elicits in vitro bladder cell invasion via the Akt signaling pathway," Oncogene, 2004, vol. 23, pp. 4745-4753.

Rudnick, S.I. et al., "Affinity and Avidity in Antibody-Based Tumor Targeting," Can. Biotherp. and Radiopharm., 2009, vol. 24, pp. 155-162.

Takeichi et al., "Cadherins: A Molecular Family Important in Selective Cell-Cell Adhesion," Annual Review of Biochemistry, 1990, vol. 59, No. 1, pp. 237-252.

(Continued)

*Primary Examiner* — Alana Harris Dent
(74) *Attorney, Agent, or Firm* — Riverside Law LLP

(57) ABSTRACT

The present application provides fully human antibodies against N-Cadherin for therapeutic and diagnostic methods in cancer.

3 Claims, 21 Drawing Sheets

(56) References Cited

OTHER PUBLICATIONS

Tanaka et al., "Monoclonal antibody targeting of N-cadherin inhibits prostate cancer growth, metastasis and castration resistance," Nature Medicine, 2010, vol. 16, No. 12, pp. 1414-1420.

Talmadge, J.E. et al., "Murine Models to Evaluate Novel and Conventional Therapeutic Strategies for Cancer," Am. J. Pathol., 2007, vol. 170, No. 3, pp. 793-804.

Thurber, G.M. et al., "Antibody tumor penetration: Transport opposed by systemic and antigen-mediated clearance," Adv. Drug Deliv. Rev., 2008, vol. 60, pp. 1421-1434.

Tomita, K. et al., "Cadherin Switching in Human Prostate Cancer Progression," Cancer Research, Jul. 1, 2000, vol. 60, pp. 3650-3654.

Voskoglou-Nomikos, T., "Clinical Predictive Value of the in vitro Cell Line, Human Xenograft, and Mouse Allograft Preclinical Cancer Models," Clin. Can. Res., 2003, vol. 9, pp. 4227-4239.

Wallerand, H. et al., "P-AKT Pathway Activation and Inhibition Depends on N-Cadherin or P-EGFR Expression in Invasive Human Bladder Cancer Cell Lines," Journal of Urology & Annual Meeting of the American-Urological-Association, San Antonion, TX, May 21-26, 2005, Abstract No. 582, 1 page.

Wallerland et al., "Phospho-Akt pathway activation and inhibition depends on N-cadherin or phospho-EGFR expression in invasive human bladder cancer cell lines," Urologic Oncology, 2010, vol. 28, No. 2, pp. 180-188.

Williams et al., "Identification of an N-cadherin Motif That Can Interact with the Fibroblast Growth Factor Receptor and Is Required for Axonal Growth," The Journal of Biological Chemistry, 2001, vol. 276, No. 47, pp. 43879-43886.

Sheets et al., "Efficient construction of a large nonimmune phage antibody library: The production of high-affinity human single-chain antibodies to protein antigens," Proceeding of the National Academy of Sciences, National Academy of Sciences, US, 1998, vol. 95, No. 11, pp. 6157-6162.

Supplementary European Search Report, Jun. 14, 2012, EP application No. 09825592.0, 14 pages.

Alexander, N.R. et al., "*N-cadherin* Gene Expression in Prostate Carcinoma is Modulated by Integrin-Dependent Nuclear Translocation of Twist1," *Cancer Research*, Apr. 1, 2006, vol. 66, No. 7, pp. 3365-3369.

Harrison, O.J. et al., "The mechanism of cell adhesion by classical cadherins: the role of domain 1," *Journal of Cell Science*, 2005, vol. 118, No. 4, pp. 711-721.

International Search Report mailed on Jul. 22, 2010, for International Application No. PCT/US2009/063881 filed on Nov. 10, 2009, 6 pages.

Kim, J-B. et al., "N-Cadherin Extracellular Repeat 4 Mediates Epithelial to Mesenchymal Transition and Increased Motility," *The Journal of Cell Biology*, Dec. 11, 2000, vol. 151, No. 6, pp. 1193-1205.

Iran, N.L. et al., "N-Cadherin Expression in Human Prostate Carcinoma Cell Lines," *American Journal of Pathology*, Sep. 1999, vol. 155, No. 3, pp. 787-798.

* cited by examiner

NF kappa B reporter assay: TAL is negative control

N-cadherin Activates NF-κB

Normal serum

DCC serum
Androgen depleted

NFkB activity after 7days treatment of 1H7, reduced slightly. This is in agreement with the western blot where pAkt and Ncad expression was reduced.

Tumor Growth Curve of LAPC9AI sort

FULLY HUMAN ANTIBODIES AGAINST N-CADHERIN

CROSS-REFERENCES TO RELATED APPLICATIONS

This application claims priority to U.S. Provisional Application Ser. No. 61/113,042, filed on Nov. 10, 2008, which is incorporated herein by reference.

STATEMENT AS TO RIGHTS TO INVENTIONS MADE UNDER FEDERALLY SPONSORED RESEARCH OR DEVELOPMENT

This invention was made with Government support of Nos. CA92131 and CA098010, awarded by the National Institutes of Health. The Government has certain rights in this invention.

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Prostate cancer is the most common malignancy and the second leading cause of cancer-related death in American men. Prostate cancer is a biologically and clinically heterogeneous disease. A majority of men with this malignancy harbor slow-growing tumors that may not impact an individual's natural lifespan, while others are struck by rapidly progressive, metastatic tumors. PSA screening is limited by a lack of specificity and an inability to predict which patients are at risk to develop hormone refractory metastatic disease. Recent studies advocating a lower PSA threshold for diagnosis may increase the number of prostate cancer diagnoses and further complicate the identification of patients with indolent vs. aggressive cancers (Punglia et al., *N Engl J Med*, 349: 335-342 (2003)). New serum and tissue markers that correlate with clinical outcome or identify patients with potentially aggressive disease are urgently needed (Welsh et al., *Proc Natl Acad Sci USA*, 100: 3410-3415 (2003)).

Recent expression profiling studies suggest that expression signatures for metastatic vs. non-metastatic tumors may reside in the primary tumor (Ramaswamy et al., *Nat Genet*, 33: 49-54 (2003); Sotiriou et al., *Proc Natl Acad Sci USA*, 100: 10393-10398 (2003)). Additional features that predispose tumors to metastasize to specific organs may also be present at some frequency in the primary tumor (Kang et al., *Cancer Cell*, 3: 537-549 (2003)). These recent observations suggest that novel markers of pre-metastatic or pre-hormone refractory prostate cancer may be identified in early stage disease. These markers may also play a role in the biology of metastatic or hormone refractory prostate cancer progression. Recent examples of genes present in primary tumors that correlate with outcome and play a role in the biology of prostate cancer progression include EZH2 and LIM kinase (Varambally et al., *Nature*, 419: 624-629 (2002); Yoshioka et al., *Proc Natl Acad Sci USA*, 100: 7247-7252 (2003)). However, neither of these two genes is secreted.

In order to identify new candidate serum or tissue markers of hormone refractory prostate cancer, we have previously compared gene expression profiles of paired hormone dependent and hormone refractory prostate cancer xenografts. The LAPC-9 xenograft was established from an osteoblastic bone metastasis and progresses from androgen dependence to independence following castration in immune deficient mice (Craft et al., *Cancer Research*, In Press (1999)). It has been used previously to identify candidate therapeutic targets in prostate cancer. Differentially expressed genes were validated and then examined for sequence homology to secreted or cell surface proteins. N-Cadherin has been identified as a marker of cancer. The identification, characterization and initial validation of N-Cadherin, which is expressed in both hormone refractory prostate cancer and bladder cancer, has been previously reported (WO/2007/109347).

One type of cell movement than can be observed in embryogenesis requires the loss of cell-cell contacts for the migration of individual cells or small group of cells through the extracellular matix. This process is called epithelial to mesenchymal transition (EMT). EMT also occurs in pathological situations, such as the acquisition of a motile and invasive phenotype of tumor cells of epithelial origin. A hallmark of EMT, is the loss of E-cadherin and the de novo expression of N-cadherin adhesion molecules. N-cadherin promotes tumor cell survival, migration and invasion, and high levels of N-cadherin expression is often associated with poor prognosis. N-cadherin is also expressed in endothelial cells and plays an essential role in the maturation and stabilization of normal vessels and tumor-associated angiogenic vessels. Increasing experimental evidence suggests that N-cadherin is a potential therapeutic target in cancer.

The function of N-cadherin has been studied at the molecular level. N-cadherin N-terminal extracellular region (160 to 724 a.a) consists of 5 domains (ECD1-ECD5). ECD1 and ECD2 are the minimal domains required for intracellular adhesion but if all extracellular domains are involved, the level of adhesion is strengthened. In addition a study has shown that a 69 amino acid portion of ECD4 was found to be essential in migration and mobility but not in cellular adhesion (Kim et al. *J Cell Biol* 2000).

Accordingly, the invention provides compositions and methods which target N-Cadherin in the diagnosis, prognosis, and treatment of cancers expressing N-Cadherin including, but not limited to, prostate cancer and bladder cancer. Antibodies, and fragments thereof, which are specific to the extracellular domains of N-cadherin, are also reported herein.

BRIEF SUMMARY OF THE INVENTION

The present application provides fully human antibodies against N-Cadherin for therapeutic and diagnostic methods in cancer, e.g., prostate and bladder cancer.

DETAILED DESCRIPTION OF THE INVENTION

Figure 1:
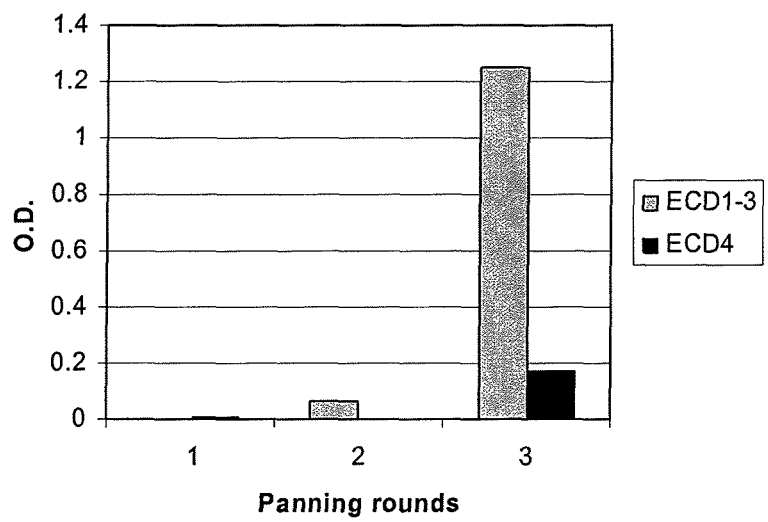
FIG. 1. Enrichment in anti-N-cadherin phage antibody through successive panning rounds.

We report here the method of treating a cancer patient and the method of identifying cancer stem cells, wherein the N-cadherin protein in the cancer cells is expressed at normal or low levels, or is expressed by a subset of cancer cells and is not overexpressed. In addition, we reported here antibodies, and fragments thereof, which are specific to the extracellular domains of N-cadherin.

N-cadherin expression can contribute to prostate and bladder cancer invasion and metastasis as well as the progression of prostate caner to hormone refractory disease. N-Cadherin can be targeted therapeutically both alone and in combination with other small molecule inhibitors of mTOR and EGFR. Targeting N-Cadherin can help prevent or control invasive and metastatic prostate cancer.

This invention relates to the discovery that N-cadherin does not need to be overexpressed compared to normal tissues to be a target for treatment and diagnosis. It can be expressed at low levels and also can be expressed only by a subset of cells. We have found that targeting N-cadherin even in 5% of prostate cancer cells is sufficient to block the progression of prostate cancers to castration resistance.

This invention also relates to N-cadherin as a target in cancer stem cells. We have found that targeting of N-cadherin in 5% or fewer cells is sufficient to block tumor progression. This discovery is consistent with the hypothesis that N-cadherin is a marker of cancer stem cells, and that inhibition of N-cadherin on these stem cells is sufficient to block growth of the tumor as a whole.

This invention further relates to the discovery that N-cadherin expressing cells, consistent with its being a cancer stem cell marker, are more tumorigenic than N-cadherin non-expresing cells. N-cadherin positive cells can give rise to N-cadherin negative cells, also consistent with the theory that N-cadherin is a novel marker of cancer stem cells. Finally, tumors must upregulate or acquire N-cadherin in order to grow. That is, tumor stem cells must acquire properties of epithelial to mesenchymal transition in order to be tumorigenic.

Accordingly, N-Cadherin is an especially promising therapeutic target. It is found on cell surfaces, expressed in many epithelial tumors, and is associated with invasion, metastasis and possibly androgen independence. Antibodies against N-cadherin therefore are a particularly preferred agent for use in treating epithelial cancers, including but not limited to urogenital cancers (bladder, prostate), and, more particularly, their invasive or metastasized forms. In some embodiments, monoclonal antibodies directed against an extracellular domain of N-cadherin are preferred. In further embodiments, the first extracellular domain (EC 1), portions of the first and second domains, first to third domains, or fourth extracellular domain of N-cadherin are preferred in treating these cancers. In some embodiments, use of a antibody directed toward the extracellular domain 4 is particularly preferred in these treatments as this domain is found to be important in pro-motility and invasive potential (see, Kim et al, *J Cell Biol.* 151(6): 1193-206 (2000), incorporated by reference in its entirety with respect to the definition of the various N-cadherin domains.

Here we describe the selection and characterization of human ScFvs specific to two independent N-cadherin recombinant proteins: N-cadherin extracellular domains one to three (ECD1-3) and N-cadherin forth domain (ECD4). The two independent screens were designed in an effort to generate specific reagents able to affect the adhesion and migration phenotype of this molecule as well as generating reagents to target N-cadherin expressing cells. Individual phage clones from the fourth panning round were characterized by ELISA and flow cytometry. Specific binders were sequenced and some of the selected clones were reformatted into small bivalent antibody fragments (diabodies). The diabodies show specific binding to N-cadherin expressing cells.

Anti-N-cadherin fragments, as described here, are the basic building block upon which can be fabricated human whole antibodies or engineered antibodies of varying shapes and sizes, the primary attribute of which is the ability to bind specifically to the N-cadherin protein. These antibodies can be used for the treatment or diagnosis of prostate, bladder or other cancers expressing the N-cadherin protein. It is important to note that N-cadherin expression in the tumor can be by the tumor cells themselves or any of the surrounding stroma (muscle, fibroblasts, blood vessels etc). We have previously shown that N-cadherin is an important biological determinant of invasion, growth, metastasis and progression of prostate, bladder and other cancers and is a critical diagnostic, prognostic, and therapeutic target. Murine monoclonal antibodies against N-cadherin are able to block tumor growth, metastasis, invasion and progression to androgen independence in animal models of cancer. The discovery of human scFV's that can easily be reformatted into whole or engineered antibodies provides the ability to target cancers without inciting an immune response against the antibodies.

To our knowledge, we describe the first human antibody fragments against N-cadherin derived with the goal of prostate and other cancer diagnosis and treatment. The invention is predicated on prior art developed by our group implicating N-cadherin in prostate and bladder and other cancer progression, as well as the concept of targeting it therapeutically. Phage display describes a well established technique for the isolation of antibody fragments. The non-immune phage library used here was developed by Dr. J D Marks at UC. San Francisco.

The invention describes the isolation and characterization of single chain fragments that recognize N-cadherin. These can be use as single chain fragments or reformatted into larger fragments, such as whole IgG, that can be used for the diagnosis or treatment of cancers.

As stated, the invention describes a number of candidate fragments with putative diagnostic and therapeutic utility that can be reformatted into larger constructs and used to recognize N-cadherin in prostate and other cancers. These antibodies can be used by themselves (naked antibodies) or conjugated to radioisotopes, nanoparticles, liposomes, virus or any other "payload" for delivery to tumors for therapy, imaging or other purpose. The fragments can be used to increase the specificity of any therapy or imaging modality for N-cadherin expressing tumors.

To our knowledge, we are the first to show that antibodies against N-cadherin have therapeutic activity, superior to any other known means of targeting such tumors. The advantage of this invention is that the antibody fragments are nonimmunogenic and human and can be used in patients without additional modification. Also, fragments recognizing N-cadherin have the advantage of flexibility, in that they can easily be engineered for almost any purpose.

Definitions

Figure 7:
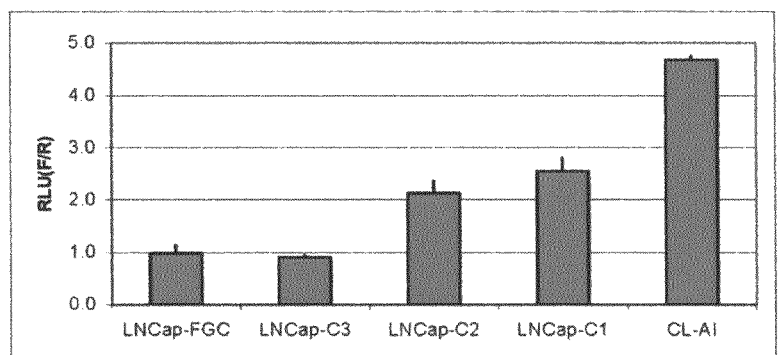
FIG. 7. N-cadherin Activates NF-κB.
Figure 7:
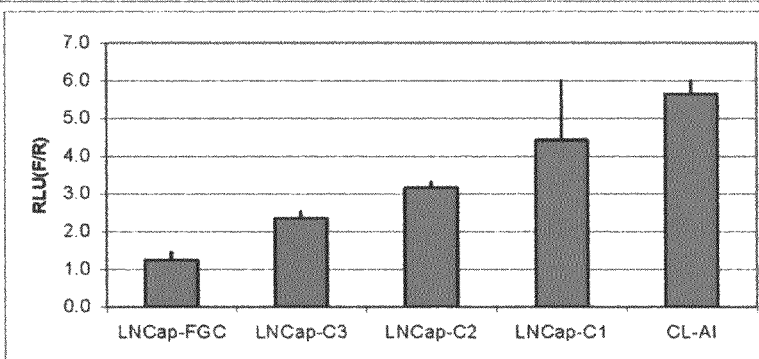
Figure 8:
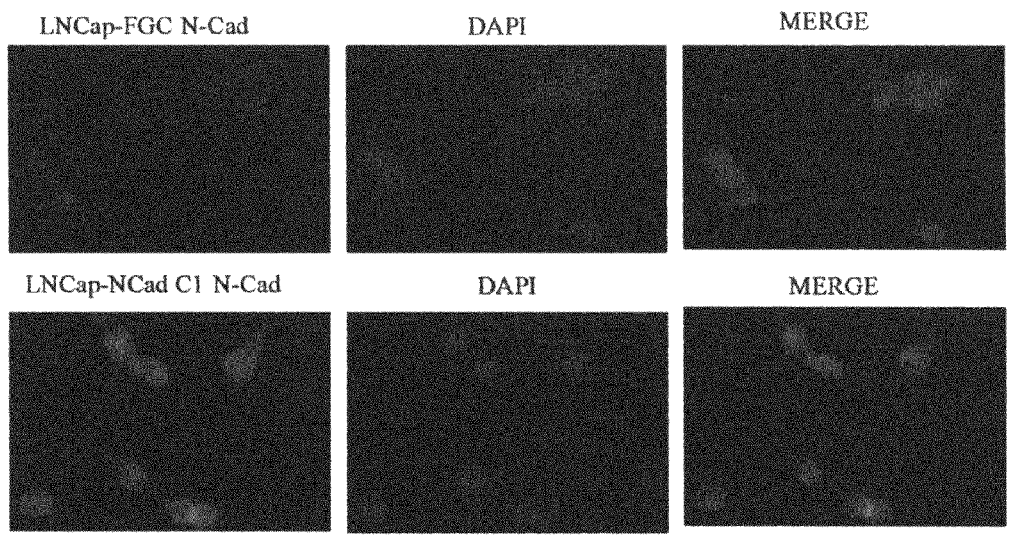
FIG. 8. N-cadherin is expressed on cell surface of C1 cells.
Figure 9:
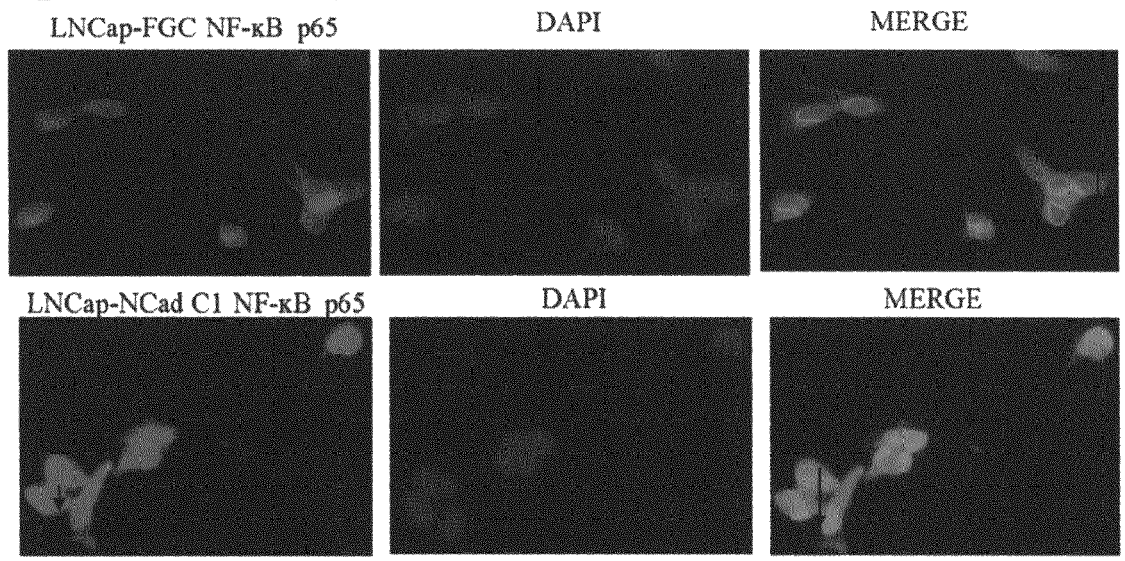
FIG. 9. NF-κB localizes to nucleus in N-Cadherin positive cells (C1).
Figure 10:
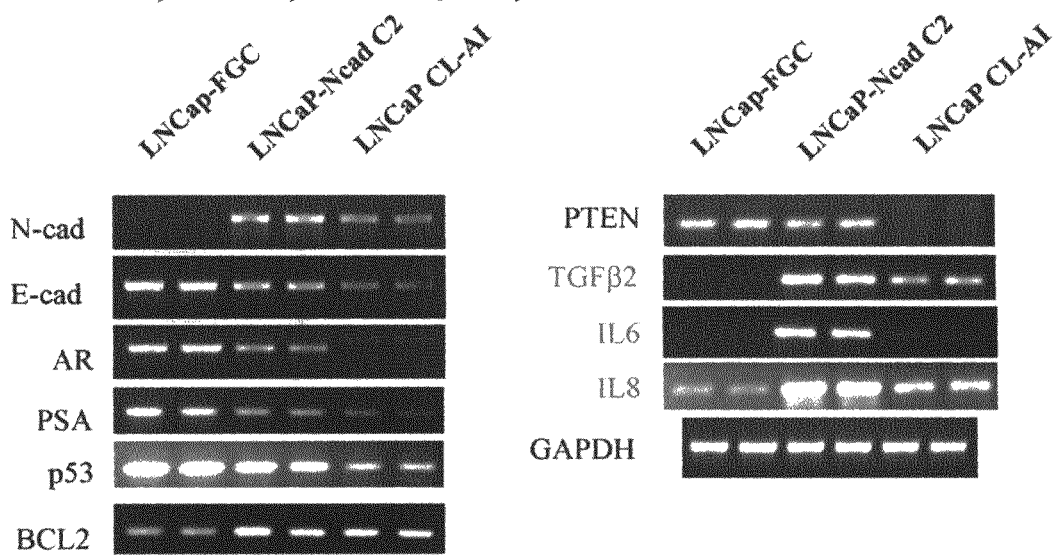
FIG. 10. N-Cadherin Expression Results in Induction of IL-6, IL-8, TGF β2, and bcl- 2.
Figure 11:
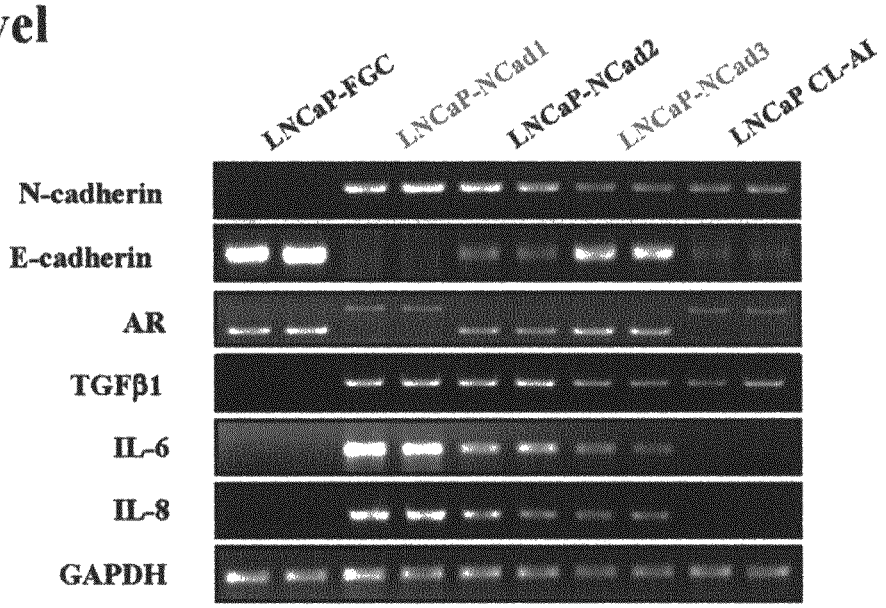
FIG. 11. Correlation of Induced Genes with N-Cadherin Level.
Figure 12:
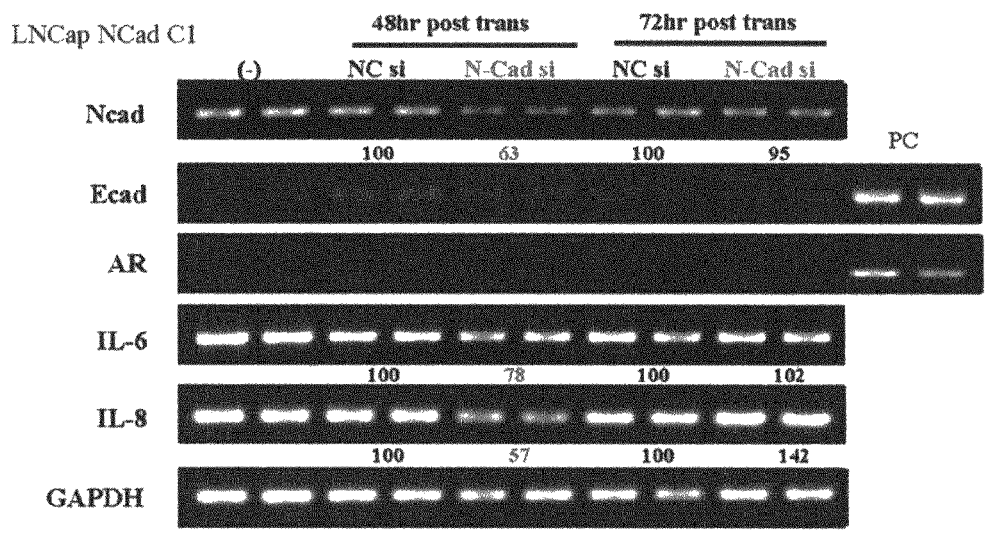
FIG. 12. N-Cadherin Knockdown Leads to Downregulation of IL-6 and IL-8.
Figure 13:
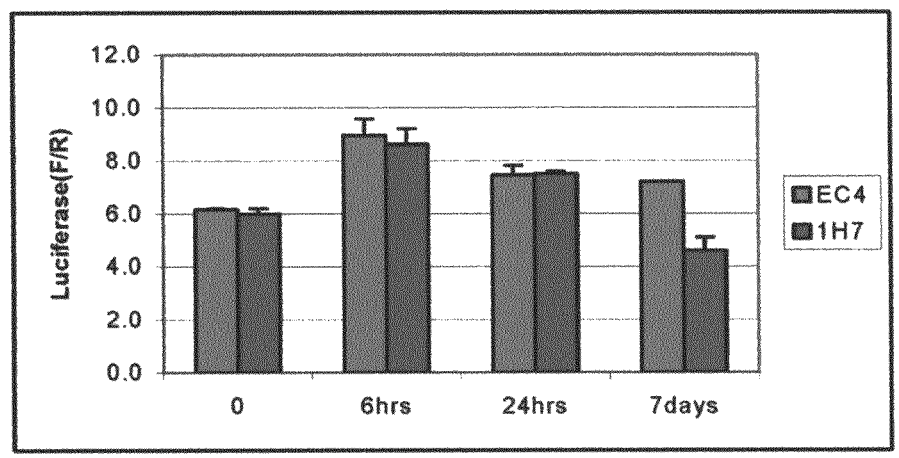
FIG. 13. NFκB activity after N-Cadherin antibodies treatment.
Figure 14:
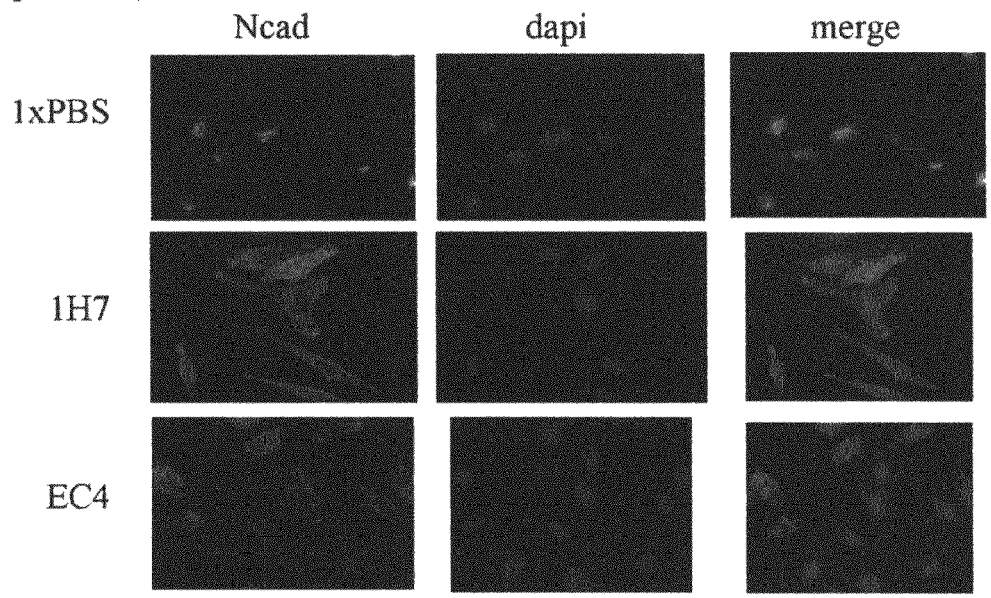
FIG. 14. Ncad in PC3 cells: 48 hr antibody incubation.
Figure 15:
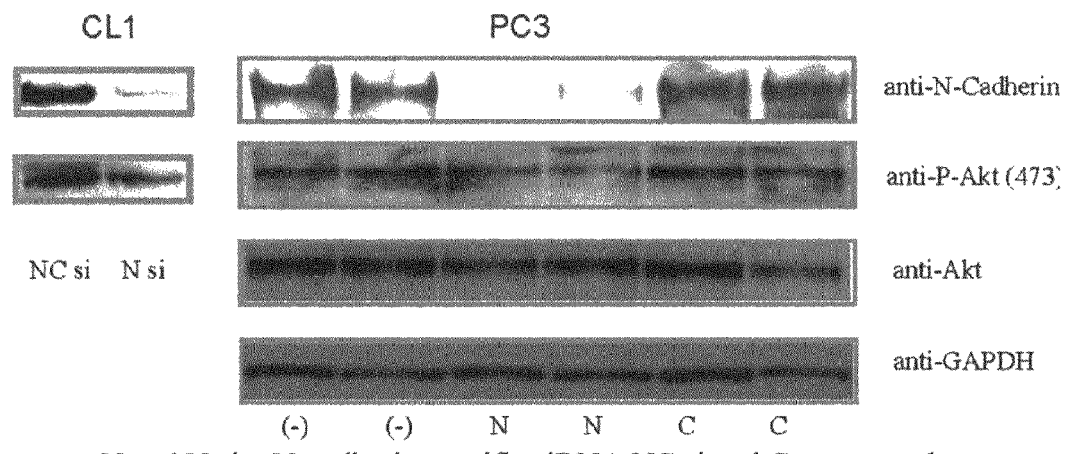
FIG. 15. N-Cadherin Knockdown Leads to Downregulation of Activated Akt.
Figure 16:
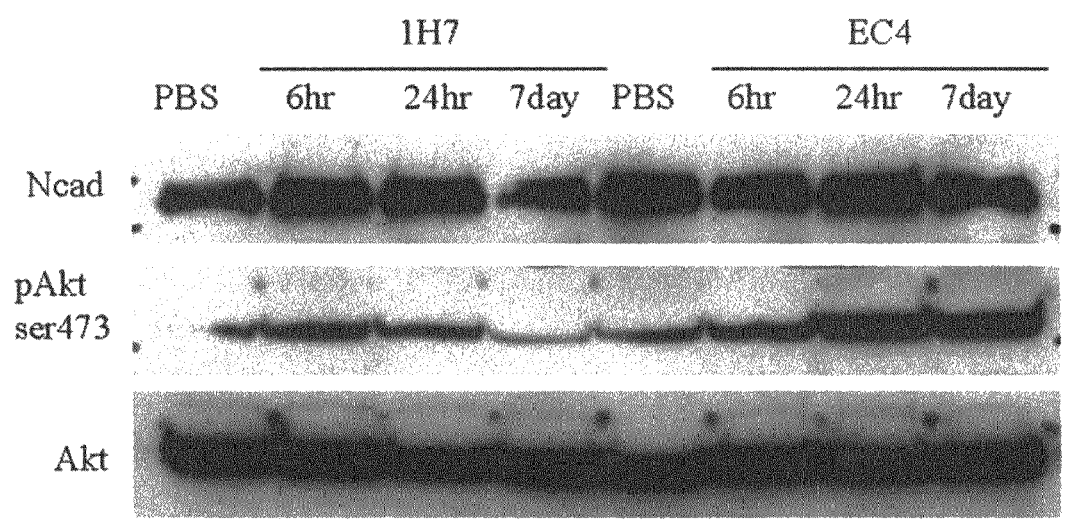
FIG. 16. N-cadherin specific antibodies activate, then downregulate Akt activation.
Figure 17:
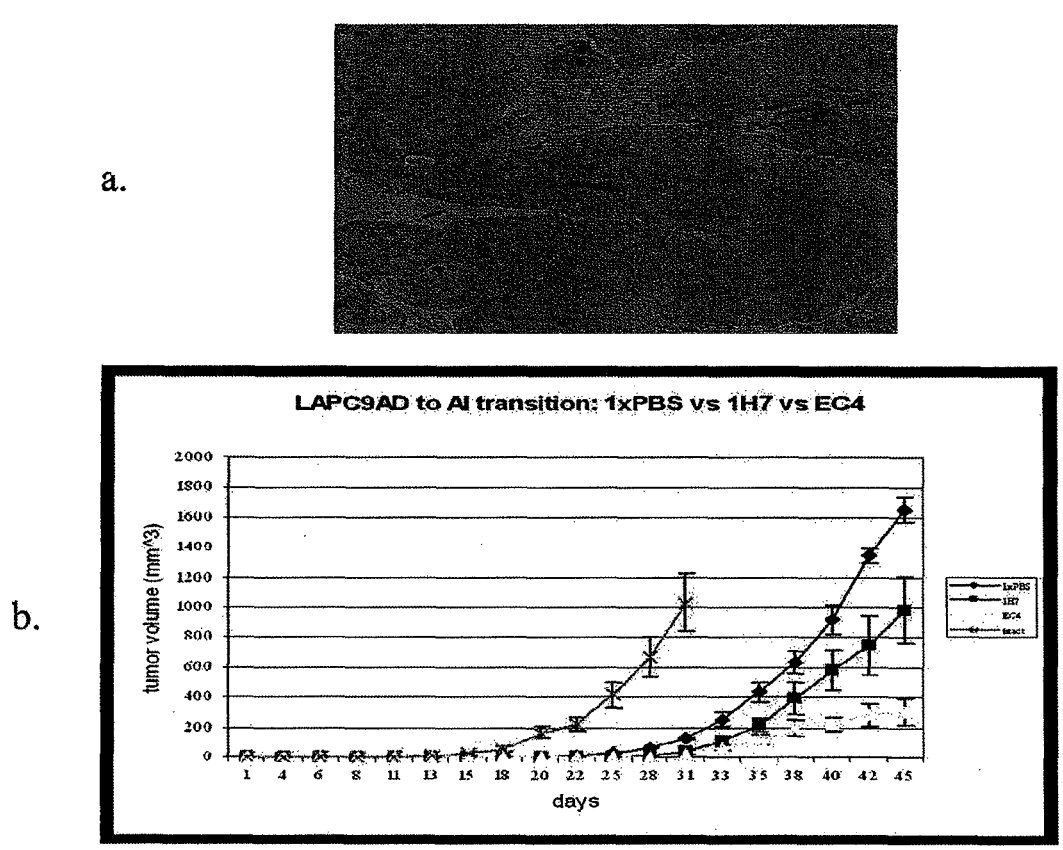
FIG. 17. LAPC9AD to AI transition: 1× PBS vs 1H7 vs. EC4.
Figure 18:
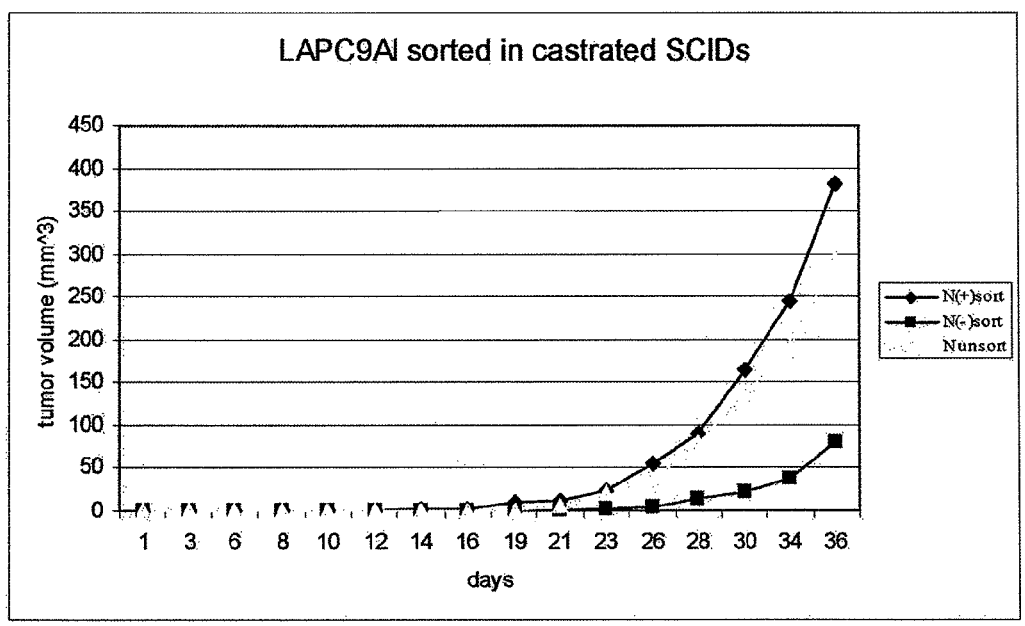
FIG. 18. Tumor growth curves of LAPCAI sorted on N-cadherin. LAPCAI sorted in castrated SCIDs.
Figure 19:
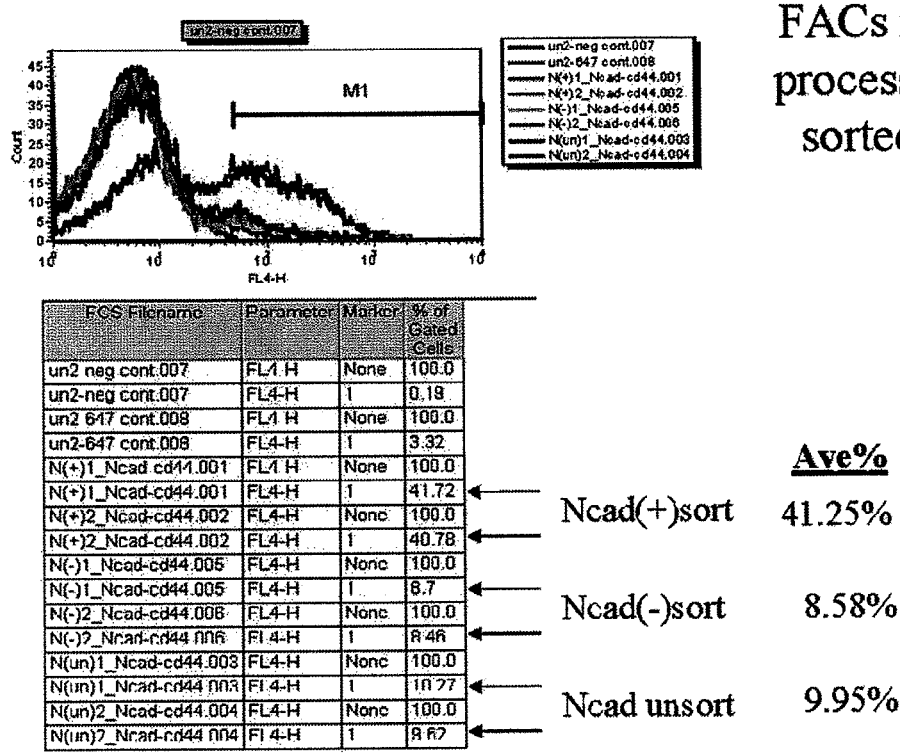
FIG. 19. FACS results on processed N-cadherin sorted tumors.
Figure 20:
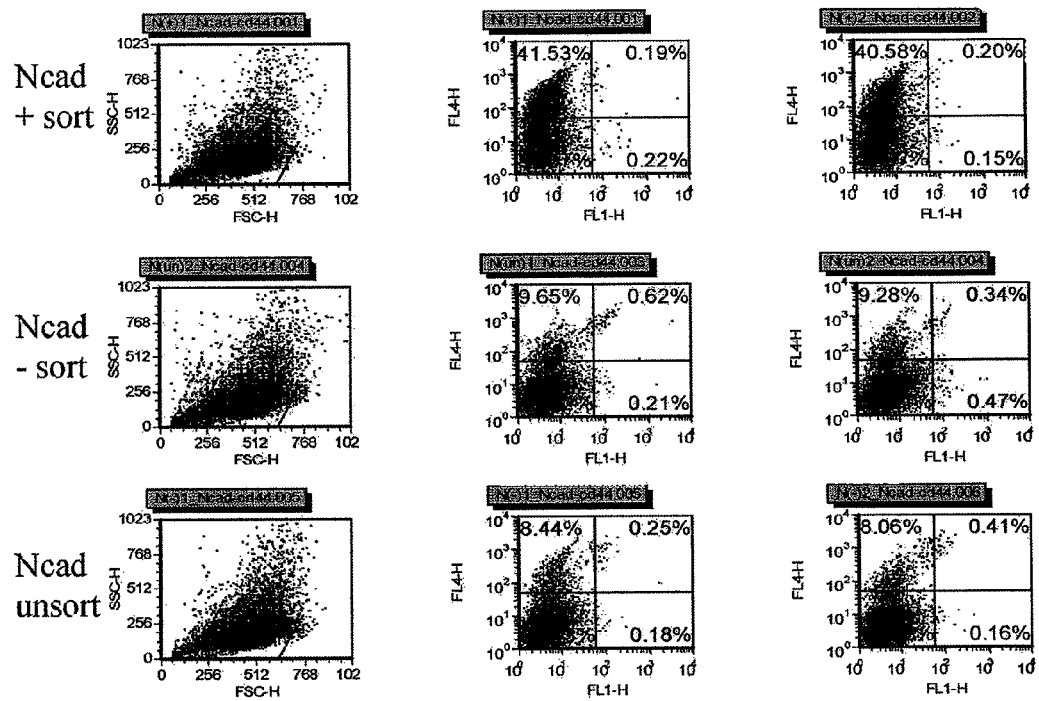
FIG. 20 Further FACS results on processed N-cadherin sorted tumors.
Figure 21:
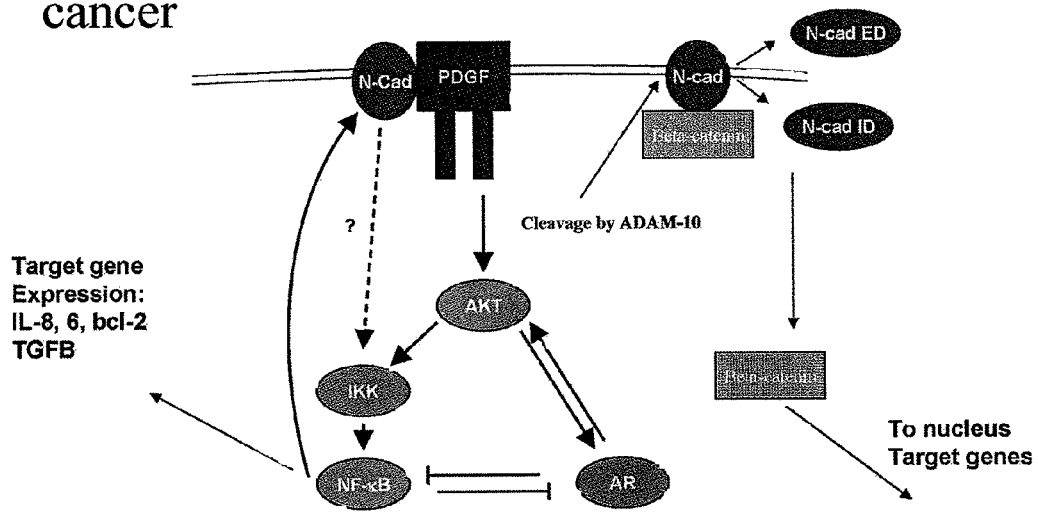
FIG. 21 Model of N-cadherin signaling in prostate cancer.

"N-Cadherin and E-Cadherin" refer to nucleic acids, e.g., gene, pre-mRNA, mRNA, and polypeptides, polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to a polypeptide encoded by a respectively referenced nucleic acid or an amino acid sequence described herein, for example, as depicted in FIGS. 7, 8, and 9, respectively; (2) specifically bind to antibodies, e.g., polyclonal antibodies, raised against an immunogen comprising a referenced amino acid sequence as depicted in FIGS. 7, 8, and 9, respectively; immunogenic fragments respectively thereof, and conservatively modified variants respectively thereof; (3) specifically hybridize under stringent hybridization conditions to a nucleic acid encoding a referenced amino acid sequence as depicted in FIGS. 7, 8, and 9, respectively, and conservatively modified variants respectively thereof; (4) have a nucleic acid sequence that has greater than about 95%, preferably greater than about 96%, 97%, 98%, 99%, or higher nucleotide sequence identity, preferably over a region of at least about 25, 50, 100, 150, 200, 250, 500, 1000, or more nucleotides, to a reference nucleic acid sequence as shown, respectively, in FIGS. 7, 8, and 9. A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules.

"Cancer" refers to human cancers and carcinomas, sarcomas, adenocarcinomas, lymphomas, leukemias, etc., including solid tumors and lymphoid cancers, kidney, breast, lung, kidney, bladder, colon, ovarian, prostate, pancreas, stomach, brain, head and neck, skin, uterine, testicular, esophagus, and liver cancer, lymphoma, including non-Hodgkin's and Hodgkin's lymphoma, leukemia, and multiple myeloma. "Urogenital cancer" refers to human cancers of urinary tract and genital tissues, including but not limited to kidney, bladder, urinary tract, urethra, prostate, penis, testicle, vulva, vagina, cervical and ovary tissues.

The cancer to be treated herein may be one characterized by excessive activation of N-cadherin. Alternatively, the cancer to be treated herein may be one where the N-cadherin protein is expressed at normal or low levels, or one where the N-cadherin protein is expressed by a subset of cells, and where the N-cadherin protein is not overexpressed. In one embodiment of the invention, a diagnostic or prognostic assay will be performed to determine whether the patient's cancer is characterized by expression of N-cadherin. Various assays for determining such amplification/express ion are contemplated and include the immunohistochemistry, FISH and shed antigen assays, southern blotting, or PCR techniques. Moreover, the N-cadherin expression or amplification may be evaluated using an in vivo diagnostic assay, e.g. by administering a molecule (such as an antibody) which binds the molecule to be detected and is tagged with a detectable label (e.g. a radioactive isotope) and externally scanning the patient for localization of the label. In some embodiments, the cancer to be treated is not yet invasive, but expresses N-cadherin.

"Therapy resistant" cancers, tumor cells, and tumors refers to cancers that have become resistant or refractory to either or both apoptosis-mediated (e.g., through death receptor cell signaling, for example, Fas ligand receptor, TRAIL receptors, TNF-R1, chemotherapeutic drugs, radiation) and non-apoptosis mediated (e.g., toxic drugs, chemicals) cancer therapies, including chemotherapy, hormonal therapy, radiotherapy, and immunotherapy.

"Overexpression" refers to RNA or protein expression of N-Cadherin, LY6-E, and E-Cadherin in a test tissue sample that is significantly higher that RNA or protein expression of N-Cadherin, LY6-E, and E-Cadherin, respectively, in a control tissue sample. In one embodiment, the tissue sample is autologous. Cancerous test tissue samples (e.g., bladder, prostate) associated with invasiveness, metastasis, hormone independent (e.g., androgen independence), or refractoriness to treatment or an increased likelihood of same typically have at least two fold higher expression of N-Cadherin or LY6-E mRNA or protein, often up to three, four, five, eight, ten or more fold higher expression of N-Cadherin, or LY6-E in comparison to cancer tissues from patients who are less likely to progress to metastasis or to normal (i.e., non-cancer) tissue samples. Such differences may be readily apparent when viewing the bands of gels with approximately similarly loaded with test and controls samples. Prostate cancers expressing increased amounts of N-Cadherin or Ly6-E are more likely to become invasive, metastasize, or progress to androgen independent or treatment refractory cancer. Various cutoffs are pertinent for N-Cadherin or Ly6-E positivity, since it is possible that a small percentage of N-Cadherin or Ly6-E positive cells in primary tumors may identify tumors with a high risk for recurrence and metastasis. The terms "overexpress," "overexpression" or "overexpressed" interchangeably refer to a gene that is transcribed or translated at a detectably greater level, usually in a cancer cell, in comparison to a normal cell. Overexpression therefore refers to both overexpression of protein and RNA (due to increased transcription, post transcriptional processing, translation, post translational processing, altered stability, and altered protein degradation), as well as local overexpression due to altered protein traffic patterns (increased nuclear localization), and augmented functional activity, e.g., as in an increased enzyme hydrolysis of substrate. Overexpression can also be by 50%, 60%, 70%, 80%, 90% or more in comparison to a normal cell or comparison cell (e.g., a BPH cell).

The terms "cancer that expresses N-Cadherin" and "cancer associated with the expression of N-Cadherin" interchangeably refer to cancer cells or tissues that express N-Cadherin in accordance with the above definition.

The terms "cancer-associated antigen" or "tumor-specific marker" or "tumor marker" interchangeably refers to a molecule (typically protein, carbohydrate or lipid) that is preferentially expressed in a cancer cell in comparison to a normal cell, and which is useful for the preferential targeting of a pharmacological agent to the cancer cell. A marker or antigen can be expressed on the cell surface or intracellularly. Oftentimes, a cancer-associated antigen is a molecule that is expressed or stabilized with minimal degradation in a cancer cell in comparison to a normal cell, for instance, 2-fold expression, 3-fold expression or more in comparison to a normal cell. Oftentimes, a cancer-associated antigen is a molecule that is inappropriately synthesized in the cancer cell, for instance, a molecule that contains deletions, additions or mutations in comparison to the molecule expressed on a normal cell. Oftentimes, a cancer-associated antigen will be expressed exclusively in a cancer cell and not synthesized or expressed in a normal cell. Exemplified cell surface tumor markers include the proteins c-erbB-2 and human epidermal growth factor receptor (HER) for breast cancer, PSMA for prostate cancer, and carbohydrate mucins in numerous cancers, including breast, ovarian and colorectal. Exemplified intracellular tumor markers include, for example, mutated tumor suppressor or cell cycle proteins, including p53.

E-cadherin is conversely typically underexpressed in cancerous tissue samples in tissue samples from cancer patients which are likely to become invasive, metastasize, or progress to androgen independent or treatment refractory cancer. This underexpression may be two-fold, three-fold, four-fold, or at least five-fold. Such differences may be readily apparent when viewing the bands of gels with approximately similarly loaded with test and controls samples. The combined N-cadherin/E-cadherin values in cancers which are likely to become invasive, metastasize, or progress to androgen independent or treatment refractory cancer, are therefore even greater and can be at least two-fold, three-fold, four-fold, five-fold, ten-fold, or twenty-fold greater. Various cutoffs are pertinent for N-Cadherin positivity/e-cadherin negativity, since it is possible that a small percentage of N-Cadherin positive cells in primary tumors may identify tumors with a high risk for recurrence and metastasis.

An "agonist" refers to an agent that binds to a polypeptide or polynucleotide of the invention, stimulates, increases, activates, facilitates, enhances activation, sensitizes or up regulates the activity or expression of a polypeptide or polynucleotide of the invention.

An "antagonist" refers to an agent that inhibits expression of a polypeptide or polynucleotide of the invention or binds to, partially or totally blocks stimulation, decreases, prevents, delays activation, inactivates, desensitizes, or down regulates the activity of a polypeptide or polynucleotide of the invention.

"Inhibitors," "activators," and "modulators" of expression or of activity are used to refer to inhibitory, activating, or modulating molecules, respectively, identified using in vitro and in vivo assays for expression or activity, e.g., ligands, agonists, antagonists, and their homologs and mimetics. The term "modulator" includes inhibitors and activators. Inhibitors are agents that, e.g., inhibit expression of a polypeptide or polynucleotide of the invention or bind to, partially or totally block stimulation or enzymatic activity, decrease, prevent, delay activation, inactivate, desensitize, or down regulate the activity of a polypeptide or polynucleotide of the invention, e.g., antagonists. Activators are agents that, e.g., induce or activate the expression of a polypeptide or polynucleotide of the invention or bind to, stimulate, increase, open, activate, facilitate, enhance activation or enzymatic activity, sensitize or up regulate the activity of a polypeptide or polynucleotide of the invention, e.g., agonists. Modulators include naturally occurring and synthetic ligands, antagonists, agonists, small chemical molecules and the like. Assays to identify inhibitors and activators include, e.g., applying putative modulator compounds to cells, in the presence or absence of a polypeptide or polynucleotide of the invention and then determining the functional effects on a polypeptide or polynucleotide of the invention activity. Samples or assays comprising a polypeptide or polynucleotide of the invention that are treated with a potential activator, inhibitor, or modulator are compared to control samples without the inhibitor, activator, or modulator to examine the extent of effect. Control samples (untreated with modulators) are assigned a relative activity value of 100%. Inhibition is achieved when the activity value of a polypeptide or polynucleotide of the invention relative to the control is about 80%, optionally 50% or 25-1%. Activation is achieved when the activity value of a polypeptide or polynucleotide of the invention relative to the control is 110%, optionally 150%, optionally 200-500%, or 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, RNAi, siRNA, antibody, oligonucleotide, etc. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 Daltons and less than about 2500 Daltons, preferably less than about 2000 Daltons, preferably between about 100 to about 1000 Daltons, more preferably between about 200 to about 500 Daltons.

Cytotoxic agents include "cell-cycle-specific" or "antimitotic" or "cytoskeletal-interacting" drugs. These terms interchangeably refer to any pharmacological agent that blocks cells in mitosis. Such agents are useful in chemotherapy. Generally, cell-cycle-specific-drugs bind to the cytoskeletal protein tubulin and block the ability of tubulin to polymerize into microtubules, resulting in the arrest of cell division at metaphase. Exemplified cell-cycle-specific drugs include vinca alkaloids, taxanes, colchicine, and podophyllotoxin. Exemplified vinca alkaloids include vinblastine, vincristine, vindesine and vinorelbine. Exemplifed taxanes include paclitaxel and docetaxel. Another example of a cytoskeletal-interacting drug includes 2-methoxyestradiol.

An "siRNA" or "RNAi" refers to a nucleic acid that forms a double stranded RNA, which double stranded RNA has the ability to reduce or inhibit expression of a gene or target gene when the siRNA expressed in the same cell as the gene or target gene. "siRNA" or "RNAi" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 or about 24-29 nucleotides in length, e.g., 20, 21, 22, 23, 24, 25, 26, 27, 28, 29, or 30 nucleotides in length.

The design and making of siRNA molecules and vectors are well known to those of ordinary skill in the art. For instance, an efficient process for designing a suitable siRNA is to start at the AUG start codon of the mRNA transcript (e.g., see, FIG. 5) and scan for AA dinucleotide sequences (see, Elbashir et al. *EMBO J* 20: 6877-6888 (2001). Each AA and the 3' adjacent nucleotides are potential siRNA target sites. The length of the adjacent site sequence will determine the length of the siRNA. For instance, 19 adjacent sites would give a 21 Nucleotide long siRNA siRNAs with 3' overhanging UU dinucleotides are often the most effective. This approach is also compatible with using RNA pol III to transcribe hairpin siRNAs. RNA pol III terminates transcription at 4-6 nucleotide poly(T) tracts to create RNA molecules having a short poly(U) tail. However, siRNAs with other 3' terminal dinucleotide overhangs can also effectively induce RNAi and the sequence may be empirically selected. For selectivity, target sequences with more than 16-17 contiguous base pairs of homology to other coding sequences can be avoided by conducting a BLAST search (see, www.ncbi.nlm.nih.gov/BLAST).

The siRNA can be administered directly or an siRNA expression vectors can be used to induce RNAi can have different design criteria. A vector can have inserted two inverted repeats separated by a short spacer sequence and ending with a string of T's which serve to terminate transcription. The expressed RNA transcript is predicted to fold into a short hairpin siRNA . The selection of siRNA target sequence, the length of the inverted repeats that encode the stem of a putative hairpin, the order of the inverted repeats, the length and composition of the spacer sequence that encodes the loop of the hairpin, and the presence or absence of 5'-overhangs, can vary. A preferred order of the siRNA expression cassette is sense strand, short spacer, and antisense strand. Hairpin siRNAs with these various stem lengths (e.g., 15 to 30) can be suitable.

The length of the loops linking sense and antisense strands of the hairpin siRNA can have varying lengths (e.g., 3 to 9 nucleotides, or longer). The vectors may contain promoters and expression enhancers or other regulatory elements which are operably linked to the nucleotide sequence encoding the siRNA. The expression "control sequences" refers to DNA sequences necessary for the expression of an operably linked coding sequence in a particular host organism.

The control sequences that are suitable for prokaryotes, for example, include a promoter, optionally an operator sequence, and a ribosome binding site. Eukaryotic cells are known to utilize promoters, polyadenylation signals, and enhancers. These control elements may be designed to allow the clinician to turn off or on the expression of the gene by adding or controlling external factors to which the regulatory elements are responsive.

Construction of suitable vectors containing the desired therapeutic gene coding and control sequences employs standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides are cleaved, tailored, and re-ligated in the form desired.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Determining the functional effect" refers to assaying for a compound that increases or decreases a parameter that is indirectly or directly under the influence of a polynucleotide or polypeptide of the invention, e.g., measuring physical and chemical or phenotypic effects. Such functional effects can be measured by any means known to those skilled in the art, e.g., changes in spectroscopic (e.g., fluorescence, absorbance, refractive index), hydrodynamic (e.g., shape), chromatographic, or solubility properties for the protein; measuring inducible markers or transcriptional activation of the protein; measuring binding activity or binding assays, e.g. binding to antibodies; measuring changes in ligand binding affinity; measurement of calcium influx; measurement of the accumulation of an enzymatic product of a polypeptide of the invention or depletion of an substrate; changes in enzymatic activity, e.g., kinase activity, measurement of changes in protein levels of a polypeptide of the invention; measurement of RNA stability; G-protein binding; GPCR phosphorylation or dephosphorylation; signal transduction, e.g., receptor-ligand interactions, second messenger concentrations (e.g., cAMP, IP3, or intracellular Ca2+); identification of downstream or reporter gene expression (CAT, luciferase, $\beta$-gal, GFP and the like), e.g., via chemiluminescence, fluorescence, colorimetric reactions, antibody binding, inducible markers, and ligand binding assays.

Samples or assays comprising a nucleic acid or protein disclosed herein that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition is achieved when the activity value relative to the control is about 80%, preferably 50%, more preferably 25-0%. Activation is achieved when the activity value relative to the control (untreated with activators) is 110%, more preferably 150%, more preferably 200-500% (i.e., two to five fold higher relative to the control), more preferably 1000-3000% higher.

"Biological sample" includes sections of tissues such as biopsy and autopsy samples, and frozen sections taken for histological purposes. Such samples include blood and blood fractions or products (e.g., serum, plasma, platelets, red blood cells, and the like), sputum, tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, Mouse; rabbit; or a bird; reptile; or fish.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (i.e., prostate, lymph node, liver, bone marrow, blood cell), the size and type of the tumor (i.e., solid or suspended (i.e., blood or ascites)), among other factors. Representative biopsy techniques include excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy" of the tumor mass, or a "fine-needle aspiration biopsy" which generally obtains a suspension of cells from within the tumor mass. Biopsy techniques are discussed, for example, in Harrison's Principles of Internal Medicine, Kasper, et al., eds., 16th ed., 2005, Chapter 70, and throughout Part V.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095-35101 (1998).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins (*1984)).

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$)

for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., John Wiley & Sons.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) PCR Protocols, A Guide to Methods and Applications, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of suitable antibodies of the invention and for use according to the invention, e.g., recombinant, monoclonal, or polyclonal antibodies, many techniques known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121: 210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein. Such effector moieties include, but are not limited to, an anti-tumor drug, a toxin, a radioactive agent, a cytokine, a second antibody or an enzyme. Further, the invention provides an embodiment wherein the antibody of the invention is linked to an enzyme that converts a prodrug into a cytotoxic agent.

The immunoconjugate can be used for targeting the effector moiety to a N-cadherin positive cell, particularly cells, which express the N-cadherin or Ly6 protein. Such differences can be readily apparent when viewing the bands of gels with approximately similarly loaded with test and controls samples. Examples of cytotoxic agents include, but are not limited to, ricin, doxorubicin, daunorubicin, taxol, ethiduim bromide, mitomycin, etoposide, tenoposide, vincristine, vinblastine, colchicine, dihydroxy anthracin dione, actinomycin D, diphteria toxin, Pseudomonas exotoxin (PE) A, PE40, abrin, and glucocorticoid and other chemotherapeutic agents, as well as radioisotopes. Suitable detectable markers include, but are not limited to, a radioisotope, a fluorescent compound, a bioluminescent compound, chemiluminescent compound, a metal chelator or an enzyme.

In some embodiments, the invention provides antibodies to N-cadherin. N-cadherin antibodies may be used systemically to treat cancer (e.g., prostate or bladder cancer) alone or when conjugated with an effector moiety. N-cadherin antibodies conjugated with toxic agents, such as ricin, as well as unconjugated antibodies may be useful therapeutic agents naturally targeted to N-cadherin -bearing prostate cancer cells. Such antibodies can be useful in blocking invasiveness. Suitable N-cadherin antibodies for use according to the invention include, but are not limited to, GC4, 1H7, 1F12, 2B3.

Additionally, the recombinant protein of the invention comprising the antigen-binding region of any of the monoclonal antibodies of the invention can be used to treat cancer.

In such a situation, the antigen-binding region of the recombinant protein is joined to at least a functionally active portion of a second protein having therapeutic activity. The second protein can include, but is not limited to, an enzyme, lymphokine, oncostatin or toxin. Suitable toxins include doxorubicin, daunorubicin, taxol, ethiduim bromide, mitomycin, etoposide, tenoposide, vincristine, vinblastine, colchicine, dihydroxy anthracin dione, actinomycin D, diphteria toxin, Pseudomonas exotoxin (PE) A, PE40, ricin, abrin, glucocorticoid and radioisotopes.

Techniques for conjugating therapeutic agents to antibodies are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery"in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)).

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Using Antibodies, A Laboratory Manual* (1998) for a description of immunoassay formats and conditions that can be used to determine specific immunoreactivity).

By "therapeutically effective dose or amount" herein is meant a dose that produces effects for which it is administered. The exact dose and formulation will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); *Remington: The Science and Practice of Pharmacy*, 20th Edition, Gennaro, Editor (2003), and Pickar, *Dosage Calculations* (1999)).

The term "pharmaceutically acceptable salts" or "pharmaceutically acceptable carrier" is meant to include salts of the active compounds which are prepared with relatively non-toxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent.

Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

Epithelial to Mesenchymal Transition (EMT) refers to the acquisition of stromal features by epithelial tumor cells. In cancer, EMT is associated with invasive and motile behavior and may be central process underlying metastasis. EMT is asssociated with poor prognosis and is mediated by multiple transcription factors, such as, SNAIL, SLUG and TWIST.

E-Cadherin is a cell surface protein involved in epithelial cell-cell adhesion which is commonly lost in invasive and metastatic solid tumors.

Detailed Embodiments

The present invention provides methods of treating a cancer patient. The methods generally comprise the steps of (a) obtaining a test tissue sample from an individual at risk of having a cancer that expresses a N-cadherin protein; (b) determining the presence or absence or amount of the N-cadherin protein in the test tissue sample in comparison to a control tissue sample from an individual known to be negative for the cancer; thereby diagnosing said cancer that expresses a N-cadherin protein, wherein the N-cadherin protein is expressed at normal or low levels, or is expressed by a subset of cells and is not overexpressed; and (c) administering an effective amount of N-cadherin antibody to the individual at risk of having a cancer that expresses a N-Cadherin protein. Typically, the tissue sample is serum, but can also be a tissue from a biopsy, particularly from a urogenital tissue including prostate tissue or bladder tissue. Usually, the antibody is a monoclonal antibody. A positive diagnosis for a cancer that expresses a N-Cadherin protein or mRNA transcript is indicated when a higher level of N-Cadherin protein is detected in a test tissue sample in comparison to a control tissue sample from an individual known not to have cancer, for example, 10%, 20%, 30%, 40%, 50%, 60%, 70%, 80%, 90%, 100%, 2-fold, 3-fold, 4-fold higher or more. The detection methods can be carried out, for example, using standard ELISA techniques known in the art (reviewed in Gosling, *Immunoassays: A Practical Approach*, 2000, Oxford University Press). Detection is accomplished by labeling a primary antibody or a secondary antibody with, for example, a radioactive isotope, a fluorescent label, an enzyme or any other detectable label known in the art.

In another embodiment, the detection methods can be carried out by contacting a test tissue sample from an patient that expresses a N-Cadherin protein or mRNA transcript with a primer set of a first oligonucleotide and a second oligonucleotide that each specifically hybridize to a N-Cadherin nucleic acid; amplifying the N-Cadherin nucleic acid in the sample; and determining the presence or absence of the N-Cadherin nucleic acid in the test tissue sample in comparison to a control tissue sample from an individual known to be negative for a cancer that expresses a N-Cadherin protein or mRNA transcript. Again, usually the tissue sample is serum, but can also be a tissue from a biopsy, particularly a urogenital tissue including a prostate or bladder tissue. A positive diagnosis for a cancer that expresses a N-Cadherin protein or mRNA transcript is indicated when a higher level of N-Cadherin transcribed RNA is detected in a test tissue sample in comparison to a control tissue sample from an individual known not to have cancer.

The methods find particular application in the treatment of prostate and bladder cancers. In certain embodiments the methods are applied to hormone refractory or therapy resistant cancers. In certain embodiments the methods are applied to metastatic cancers. For example comparisons of differential expression of a N-Cadherin protein and/or mRNA can be used to determine the stage of cancer of an individual having a cancer that expresses a N-Cadherin protein or mRNA transcript.

Treatment will generally involve the repeated administration of the anti-N-Cadherin antibodies via an acceptable route of administration such as intravenous injection (IV), at an effective dose. Dosages will depend upon various factors generally appreciated by those of skill in the art, including without limitation the type of cancer and the severity, grade, or stage of the cancer, the binding affinity and half life of the agents used, the degree of N-Cadherin expression in the patient, the extent of circulating shed N-Cadherin antigen, the desired steady-state antibody concentration level, frequency of treatment, and the influence of chemotherapeutic agents used in combination with the treatment method of the invention. Typical daily doses may range from about 0.1 to 100 mg/kg. Doses in the range of 10-500 mg of the mAb per week may be effective and well tolerated, although even higher weekly doses may be appropriate and/or well tolerated. The principal determining factor in defining the appropriate dose is the amount of a particular agent necessary to be therapeutically effective in a particular context. Repeated administrations may be required in order to achieve tumor inhibition or regression. Initial loading doses may be higher. The initial loading dose may be administered as an infusion. Periodic maintenance doses may be administered similarly, provided the initial dose is well tolerated.

Direct administration of the agents is also possible and may have advantages in certain contexts. For example, for the treatment of bladder carcinoma, the agents may be injected directly into the bladder. Because agents administered directly to bladder will be cleared from the patient rapidly, it may be possible to use non-human or chimeric antibodies effectively without significant complications of antigenicity.

In some embodiments, the invention provides a method of treating cancer, particularly a cancer which expresses N-Cadherin, or of inhibiting the growth of a cancer cell expressing a N-Cadherin protein by treating a subject or contacting the cancer cell with an antibody or fragment thereof that recognizes and binds the N-Cadherin protein in an amount effective to inhibit the growth of the cancer cell. In some embodiments, the cancer cell is a prostate cancer cell or a bladder cancer cell. The contacting antibody can be a monoclonal antibody and/or a chimeric antibody. In some embodiments, the chimeric antibody comprises a human immunoglobulin constant region. In some embodiments, the antibody is a human antibody or comprises a human immunoglobulin constant region. In further embodiments, the antibody fragment comprises an Fab, F(ab)$_2$, or Fv. In other embodiments, the fragment comprises a recombinant protein having an antigen-binding region.

In any of the embodiments above, a chemotherapeutic drug and/or radiation therapy can be administered further. In some embodiments, the patient also receives hormone antagonist therapy. The contacting of the patient with the antibody or antibody fragment, can be by administering the antibody to the patient intravenously, intraperitoneally, intramuscularly, intratumorally, or intradermally. In some embodiments, the patient has a urogenital cancer (e.g., bladder cancer, prostate cancer). In some embodiments of the above, the patient suffers from prostate cancer and optionally further receives patient hormone ablation therapy. In some embodiments, the contacting comprises administering the antibody directly into the cancer or a metastasis of the cancer.

In some embodiments, the invention provides a method of treating a cancer patient. The method generally comprises (a) obtaining a test tissue sample from an individual at risk of having a cancer that expresses a N-cadherin protein; (b) determining the presence or absence or amount of the N-cadherin protein in the test tissue sample in comparison to a control tissue sample from an individual known to be negative for the cancer; thereby diagnosing the cancer that expresses a N-cadherin protein, wherein the N-cadherin protein is expressed at normal or low levels, or is expressed by a subset of cells and is not overexpressed; (c) determining whether a cancer is likely to become invasive, metastasize, hormone independent, or refractory treatment; (d) administering a chemotherapeutic agent, an immunotherapeutic agent, hormonal therapy, or radiotherapy according to whether there is an increased likelihood of the cancer becoming invasive, metastasizing, hormone independent, or refractory to treatment.

In some embodiments, the chemotherapeutic agent can be selected from the group consisting of ricin, ricin A-chain, doxorubicin, daunorubicin, taxol, ethiduim bromide, mitomycin, etoposide, tenoposide, vincristine, vinblastine, colchicine, dihydroxy anthracin dione, actinomycin D, diphteria toxin, Pseudomonas exotoxin (PE) A, PE40, abrin, arbrin A chain, modeccin A chain, alpha-sarcin, gelonin mitogellin, retstrictocin, phenomycin, enomycin, curicin, crotin, calicheamicin, sapaonaria officinalis inhibitor, maytansinoids, and glucocorticoidricin.

The invention further provides methods of identifying cancer stem cells. The methods generally comprise (a) obtaining a test tissue sample from an individual at risk of having a cancer that expresses a N-cadherin protein; (b) determining the presence or absence of cancer stem cells in the test tissue sample in comparison to a control tissue sample from an individual known to be negative for the cancer; wherein the N-cadherin protein is expressed at normal or low levels, or is expressed by a subset of the stem cells and is not overexpressed.

In some embodiments, the invention comprises a monoclonal antibody or fragment thereof capable of binding to extracellular domain 4 of N-cadherin, comprising the amino acid sequence:

```
SEQ ID NO:1:
MAQVQLVQSGGGLAQPGGSLRLSCAASGFTFSRHAMIWVRQAPGKGLEWV

SSISGSSDSTSYADSVKGRFTISRDNSKNTLYLQMNTLRAEDTAVYYCAK

ATGYSYYYGMDVWGPGTTVTVSSGGGGSGGGGSGGGGSDIQMTQSPSSLS

ASLGDRVTITCRASQGISNYLAWYQQKPGKAPKLLIYGATTLQHGVPSRF

SGSGSGTDFSLTISSLQPEDFAIYFCQQAHSFPPTFGGGTKLEIKR
```

In some embodiments, the invention comprises a monoclonal antibody or fragment thereof capable of binding to extracellular domains 1-3 of N-cadherin, comprising the amino acid sequence selected from the groups of:

```
SEQ ID NO:2:
MAQVQLVQSGAEVKKPGASVKVSCQASGYTFTSYYIHWVRQAPGQGFEWM

GIINPSGGSASYAQKFQGRVTMTRDTSTSTVYMELRSLR

SEQ ID NO:3:
MAQVQLQESGWYFDLWGRGTPVTVSSGGGGSGGGGSGGGGSEIVLTQSPS

SLSASVGDRVTITCRASQGIRNDLGWYQQKPGKAPKLLIYAASSLQSGVP

SRFSGSGSGTDFTLTISSLQPEDFATYYCLQDYNGWTFGQGTKVEIKR

SEQ ID NO:4:
MAQVQLVESGGGVVQPGRSLRLSCAASGFSFSNYGMHWVRQAPGKGLEWV

AVISYDGRVKSYADAVKGRFTISRDNSENILYVQIDSLRVEDTAVYYCAR

RGGDHAAGMDVWGQGTTVTVSSGGGGSGGGGSGGGGSQSALTQPASVSGS

PGQSITISCTGGRSDIGGYNYVSWYQQHPGKAPKLMIYDVGNRPSGVSNR

FSGSKSGNT

SEQ ID NO:5:
MAPGAAGGVGGGVVQPGRSLRLSCAASGFTFSSYGMHWVRQAPGKGLEWV

AVISYDGSNKYYADSVKGRFTISRDNSKNTLYLQMNSLRAEDTXVYYCAR

LEYSSSSRAFDVWGQGTTVTVSSGGGGSGGGGSGGGGSSELTQDPAVSVA
```

```
LGQTVRITCQGDSLRSYYASWYQQKPGQAPVLVIYGKNNRPSGIPDRFSG

SSSGNTASLTITGAQAEDEADYYCNSRDSSGNHVVFGGGTKLTVLG

SEQ ID NO:6:
MAQVQLVESGGGVVQPGRSLRLSCAASGF

SEQ ID NO:7:
MAQVQLVQSGAEVKRPGASVRISCKASGYPFTTYPIHWVRQAPGQGLEWM

GGINPNSGATKNVQKFQGRVTMTADTSIRTAYMELSRLTSDDTAVYYCAR

GEGDTGSYLGGYWGLGTLVTVSSGGGGSGGGGSGGGGSSELTQDPAVSVA

LGQTVRITCQGDSLRSYYASWYQQKPGRAPLLVIYGKNIRPSGIPDRFSG

SSSGNSASLTITGAQAEDEADYYCNSRDRSGNYLFGVGTKVTVLG

SEQ ID NO:8:
MAQVQLVQSGAEVKKPGESLEISCKGSGYSFANNWIGWVRQMPGKGLEWM

GSIYPGDSDVRYSRSFQGHVTISADKSISTAYLQWSSLKASDTAMYYCAR

HRVAYSGYDAFDIWGQGTMVTVSSGGGGSGGGGSGGGGSSVLTQDPAVSV

ALGQTVRITCQGDSLRSYYPSWYQQKPGQAPVLVIYGKNNRPSGIPDRFS

GSSSGNTASLTITGAQAEDEADYYCHSRDRSGNQVLFGGGTKVTVLG

SEQ ID NO:9:
MAQVQLVQSGGGVVQPGRSLRLSCAASGFTFSSYGMHWVRQAPGKGLEWV

AVIWYDGSNKYYADSVKGRFTISRDNSKNTLYLQMNSLRAEDTAVYYCAR

VGGEGGVWGQGTTVTVSSGGGGSGGGGSGGGGSDIVMTQSPSTLSAS
```

In some embodiments, this invention provides antibody fragments capable of binding to extracellular domains 1-3 of N-cadherin or extracellular domains 4 of N-cadherin, wherein the fragment is a scFv. In some embodiments, this invention provides antibody fragments capable of binding to extracellular domains 1-3 of N-cadherin or extracellular domains 4 of N-cadherin, wherein the fragment is a diabody. To generate diabodies the linker SGGGGSGGGGSGGGGS (SEQ ID NO:10) was replaced by SGGGGS (SEQ ID NO:11).

Methods of Administration and Formulation

The anti-N-cadherin antibodies or immunoconjugates are administered to a human patient in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred. The administration may be local or systemic.

The compositions for administration will commonly comprise an agent as described herein (e.g., N-cadherin inhibitors, N-cadherin antibodies and immunoconjugates, N-cadherin siRNA and vectors thereof) dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

Thus, a typical pharmaceutical composition for intravenous administration will vary according to the agent. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that antibodies when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

Pharmaceutical formulations, particularly, of the antibodies and immunoconjugates and inhibitors for use with the present invention can be prepared by mixing an antibody having the desired degree of purity with optional pharmaceutically acceptable carriers, excipients or stabilizers. Such formulations can be lyophilized formulations or aqueous solutions. Acceptable carriers, excipients, or stabilizers are nontoxic to recipients at the dosages and concentrations used. Acceptable carriers, excipients or stabilizers can be acetate, phosphate, citrate, and other organic acids; antioxidants (e.g., ascorbic acid) preservatives low molecular weight polypeptides; proteins, such as serum albumin or gelatin, or hydrophilic polymers such as polyvinylpyllolidone; and amino acids, monosaccharides, disaccharides, and other carbohydrates including glucose, mannose, or dextrins; chelating agents; and ionic and non-ionic surfactants (e.g., polysorbate); salt-forming counter-ions such as sodium; metal complexes (e. g. Zn-protein complexes); and/or non-ionic surfactants. The antibody can be formulated at a concentration of between 0.5-200 mg/ml, or between 10-50 mg/ml.

The formulation may also provide additional active compounds, including, chemotherapeutic agents, cytotoxic agents, cytokines, growth inhibitory agent, and anti-hormonal agent. The active ingredients may also prepared as sustained-release preparations (e.g., semi-permeable matrices of solid hydrophobic polymers (e.g., polyesters, hydrogels (for example, poly (2-hydroxyethyl-methacrylate), or poly (vinylalcohol)), polylactides. The antibodies and immunocongugates may also be entrapped in microcapsules prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nano-particles and nanocapsules) or in macroemulsions.

The compositions can be administered for therapeutic or prophylactic treatments. In therapeutic applications, compositions are administered to a patient suffering from a disease (e.g., cancer) in a "therapeutically effective dose." Amounts effective for this use will depend upon the severity of the disease and the general state of the patient's health. Single or multiple administrations of the compositions may be administered depending on the dosage and frequency as required and tolerated by the patient. A "patient" or "subject" for the purposes of the present invention includes both humans and other animals, particularly mammals. Thus the methods are applicable to both human therapy and veterinary applications. In the preferred embodiment the patient is a mammal, preferably a primate, and in the most preferred embodiment the patient is human. Other known cancer therapies can be used in combination with the methods of the invention. For example, the compositions for use according to the invention may also be used to target or sensitize a cell to other cancer therapeutic agents such as SFU, vinblastine, actinomycin D, cisplatin, methotrexate, and the like.

In other embodiments, the methods of the invention with other cancer therapies (e.g., radical prostatectomy), radiation therapy (external beam or brachytherapy), hormone therapy (e.g., orchiectomy, LHRH-analog therapy to suppress testosterone production, anti-androgen therapy), or chemotherapy. Radical prostatectomy involves removal of the entire prostate gland plus some surrounding tissue. This treatment is used commonly when the cancer is thought not to have spread beyond the tissue. Radiation therapy is commonly used to treat prostate cancer that is still confined to the prostate gland, or has spread to nearby tissue. If the disease is more advanced, radiation may be used to reduce the size of the tumor. Hormone therapy is often used for patients whose prostate cancer has spread beyond the prostate or has recurred. The objective of hormone therapy is to lower levels of the male hormones, androgens and thereby cause the prostate cancer to shrink or grow more slowly. Luteinizing hormone-releasing hormone (LHRH) agonists decrease the production of testosterone. These agents may be injected either monthly or longer. Two such analogs are leuprolide and goserelin. Anti-androgens (e.g., flutamide, bicalutamide, and nilutamide) may also be used. Total androgen blockade refers to the use of anti-androgens in combination with orchiectomy or LHRH analogs, the s combination is called. Chemotherapy is an option for patients whose prostate cancer has spread outside of the prostate gland and for whom hormone therapy has failed. It is not expected to destroy all of the cancer cells, but it may slow tumor growth and reduce pain. Some of the chemotherapy drugs used in treating prostate cancer that has returned or continued to grow and spread after treatment with hormonal therapy include doxorubicin (Adriamycin), estramustine, etoposide, mitoxantrone, vinblastine, and paclitaxel. Two or more drugs are often given together to reduce the likelihood of the cancer cells becoming resistant to chemotherapy. Small cell carcinoma is a rare type of prostate cancer that is more likely to respond to chemotherapy than to hormonal therapy.

In some embodiments, a "cardioprotectant" is also administered with the N-cadherin antibody, N-cadherin binding inhibitor, or N-cadherin siRNA molecule for use to according to the invention (see, U.S. Pat. No. 6,949,245). A cardioprotectant is a compound or composition which prevents or reduces myocardial dysfunction (i.e. cardiomyopathy and/or congestive heart failure) associated with administration of a drug, such as an anthracycline antibiotic to a patient. The cardioprotectant may, for example, block or reduce a free-radical-mediated cardiotoxic effect and/or prevent or reduce oxidative-stress injury. Examples of cardioprotectants encompassed by the present definition include the iron-chelating agent dexrazoxane (ICRF-187) (Seifert et al. The Annals of Pharmacotherapy 28:1063-1072 (1994)); a lipid-lowering agent and/or anti-oxidant such as probucol (Singal et al. J. Mol. Cell Cardiol. 27:1055-1063 (1995)); amifostine (aminothiol 2-[(3-aminopropyl)amino]ethanethiol-dihydrogen phosphate ester, also called WR-2721, and the dephosphorylated cellular uptake form thereof called WR-1065) and S-3-(3-methylaminopropylamino)propylphosphoro-thioic acid (WR-151327), see Green et al. Cancer Research 54:738-741 (1994); digoxin (Bristow, M. R. In: Bristow M R, ed. Drug-Induced Heart Disease. New York: Elsevier 191-215 (1980)); beta-blockers such as metoprolol (Hjalmarson et al. Drugs 47:Suppl 4:31-9 (1994); and Shaddy et al. Am. Heart J. 129:197-9 (1995)); vitamin E; ascorbic acid (vitamin C); free radical scavengers such as oleanolic acid, ursolic acid and N-acetylcysteine (NAC); spin trapping compounds such as alpha-phenyl-tert-butyl nitrone (PBN); (Paracchini et al., Anticancer Res. 13:1607-1612 (1993)); selenoorganic compounds such as P251 (Elbesen); and the like.

101101 The combined administrations contemplates coadministration, using separate formulations or a single pharmaceutical formulation, and consecutive administration in either order, wherein preferably there is a time period while both (or all) active agents simultaneously exert their biological activities.

Molecules and compounds identified that indirectly or directly modulate the expression and/or function of a N-cadherin protein can be useful in treating cancers that, respectively, express N-cadherin. N-cadherin protein modulators can be administered alone or co-administered in combination with conventional chemotherapy, radiotherapy or immunotherapy as well as currently developed therapeutics.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

Preferred pharmaceutical preparations deliver one or more active N-cadherin protein modulators, optionally in combination with one or more chemotherapeutic agents or immunotherapeutic agents, in a sustained release formulation. Typically, the N-cadherin modulator is administered therapeutically as a sensitizing agent that increases the susceptibility of tumor cells to other cytotoxic cancer therapies, including chemotherapy, radiation therapy, immunotherapy and hormonal therapy.

In therapeutic use for the treatment of cancer, the N-cadherin modulators or inhibitors utilized in the pharmaceutical method of the invention are administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of cancer diagnosed in a particular patient. The dose administered to a patient, in the context of the present invention should be sufficient to effect a beneficial therapeutic response in the patient over time. The size of the dose also will be determined by the existence, nature, and extent of any adverse side-effects that accompany the administration of a particular vector, or transduced cell type in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

The pharmaceutical preparations (e.g., N-cadherin siRNAs, N-cadherin antibodies, N-cadherin vaccines, N-cadherin inhibitors, and immunoconjugates) for use according to the invention are typically delivered to a mammal, including humans and non-human mammals.

Non-human mammals treated using the present methods include domesticated animals (i.e., canine, feline, murine, rodentia, and lagomorpha) and agricultural animals (bovine, equine, ovine, porcine).

EXAMPLES

The following examples are offered to illustrate, but not limit the claimed invention.

Example 1

Isolation and Characterization of Human ScFvs Specific to Human N-Cadherin

Materials and Methods
N-Cadherin Recombinant Protein Expression and Cell Lines.

Two independent N-cadherin recombinant proteins were generated (Z Wainberg); N-cadherin extracellular domains one to three (ECD1-3) and N-cadherin forth domain (ECD4). cDNA sequence was cloned using RT- PCR from mRNA preparation. Nucleic acid 160 to 497 for ECD1-3 and nucleic acid 489 to 603 were cloned into bacterial system of expression in frame with an 6 histidine (SEQ ID NO:12) tag and in a vector in frame with an GST tag. Expression was induced with hours after induction the periplasmic fraction was isolated and recombinant protein purified using Ni-NTA chromatography. The protein was analyzed on SDS-PAGE for size and purity. LNCap N-cadherin transfected cells were generated. The complete N-cadherin cDNA was cloned into the vector and tranfected into LNCap by infection. PC3 cells and DU145, two prostate cell lines, were used to characterize the anti-N-cadherin antibody fragments isolated.

Phage Library Panning

We panned a non immune phage library displaying human single-chain Fv (scFv), containing $8.2 \times 10^8$ members generated in JD Marks laboratory as described previously (Sheets M.D. PNAS 1998). Phages were affinity-selected to N-cadherin recombinant proteins. ECD1-3 and ECD4 were separately absorbed onto two immunotubes (Nunc). The immunotubes were then washed with PBS, blocked with 4% milk in PBS at room temperature for 2 hours then washed 3 times with PBS. lml aliquots of the phage-displayed scFv library ($8.10^{11}$ pfu) were mixed with 1 ml 8% MPBS and added to the antigen-coated immunotubes. Immunotubes were incubated 1 hour at room temperature. Immunotubes were then washed once with 0.05% Tween 20 in PBS and three times with PBS. Phage were eluted with lml of 100 mM triethylamine for 5 minutes and neutralized with 0.5 ml of 1 M Tris-Hcl pH 7.4. Half the eluted phage for each rounds was frozen while the other half was used to infect TG1 cells. Phage amplification and purification were carried out as previously described (Sheets M. D. PNAS 1998). Selection included another 3 rounds of panning similar to the first round. 2 ml of 40 μl/ml was used to coat immunotubes for rounds 1 and 2, while 20 μl/ml μl/ml was used to coat immunotubes for round 3 and 4. The numbers of washes progressively increased in round 2, 3 and 4. Polyclonal phage antibodies from round 1, 2, 3 and individual 95 clones from the $4^{th}$ round of panning were evaluated by ELISA as previously described (ref Marks J D J Mol Biol. 1991 Dec 5;222(3):581-97.).

ELISA Screening of Individual Clones

The binding of 95 individual phage clones to their target was determined by ELISA (Marks J D J Mol Biol. 1991 Dec 5;222(3):581-97) (Poul M, et al. JMB Volume 301, Issue 5, Pages 1149-1161). The target used for selection was used to coat a 96 wells ELISA plate. The number of unique scFv was determined by fingerprinting the scFv genes with the restriction enzyme BstNI and confirmed by DNA sequencing.

Reformating scFvs into Diabodies.

ScFv insert were cut out of the pHEN1 using NcoI and NotI restriction enzymes and cloned into the pSyn vector using the same restriction enzyme sites. To reformat scFv into diabody the linker from 15 to 5 a.a using splicing by overlapping extension PCR (SOE-PCR) (Yazaki P J, et al. PEDS 2004 May;17(5):481-9). SOE-PCR products were cloned into the TOPO vector (invitrogen) and sequenced to verify that no mutations were generated from the PCR. The diabody constructs were finally cloned into the pSyn1 vector using NcoI and NotI restriction sites.

Expression and Purification of scFvs and Diabodies.

ScFvs and diabodies cloned into pSyn1 were transfected into TG1 bacteria for protein expression. Bacteria were grown to a density of 0.5 $O.D_{600nm}$ before the expression was induced with 1mM IPTG. After four hours of induction the bacteria were spun down and the periplasmic fraction prepared. 6HIS (SEQ ID NO:12) tag proteins were purified on a Ni-NTA column. The eluted protein was dialyzed against PBS concentrated and filtered.

Biochemical Characterization

Purified proteins were analyzed by SDS-PAGE under non-reducing conditions. Native structural size was determined by size exclusion columns (Superdex 75) (Pharmacia).

Flow Cytometry

Flow cytometry was conducted to assess binding of phage antibody clones and diabodies to cellular N-cadherin. For phage antibody staining supernatant concentrated 20 times was used. Individual clones were grown in 20 ml 2 TY to a density of 0.5 $O.D_{600\,nm}$ when phage were rescued with helper phages. After an overnight culture, monoclonal phage were harvested from the supernatant by precipitation with PEG/NaCl and resuspended in 1 ml PBS/1% BSA. For flow cytometry staining, $5 \times 10^5$ cells were incubated for one hour on ice with 100 µl of 20× PEG concentrated phage antibody clone. Cells were washed in flow buffer (PBS 1% FBS, 1 mM EDTA, 0.02% Sodium azide) and the phage antibody clones detected with monoclonal anti-M13 antibody (Amersham Biosciences). Cells were washed and stained with R-PE congugated anti-mouse antibody. For diabody staining, $5 \times 10^5$ cells were incubated for one hour on ice with the diabody at a 2 µg/ml concentration in flow buffer. Cells were washed and the diabody detected with 1/100 anti-c-Myc-biotin antibody in flow buffer. Cells were finally washed and stained with 1/40 Streptavidin-R-PE (SIGMA) in flow buffer.

In Vivo Studies

D4Db protein was labeled with $^{124}I$ and injected in the tail vein of SCID mice bearing LAPC9 AI tumors and nude mice bearing PC3 tumors. MicroPET imaging was performed 4 and 20 hours post injection. Biodistribution was performed 20 hours post injection.

Panning

The same non immune phage library displaying human single-chain Fv antibodies (scFv), containing $8.2 \times 10^8$ members were panned against ECD1-3-6His or ECD4-6HIS recombinant protein independently. Panning results including input, output, recovery and enrichment are presented in Table 1. Panning against ECD1-3 resulted in early enrichment starting from round 2, whilst enrichment only became superior to one at the last panning round for ECD4. These results are consistent with the polyclonal ELISA as a signal appeared at the second panning round with ECD1-3 while only the third panning round sample with ECD4 showed a signal.

As shown in FIG. 1, polyclonal Phage antibody from panning rounds 1, 2 and 3 were analyzed by ELISA. The targets used for panning rounds were used to coat the ELISA plate. Binding of phage antibody were detected with HRP conjugated anti-M13 antibody.

TABLE 1

|  | Immobilized protein | Input (pfu) | Output (pfu) | Recovery | Enrichment |
|---|---|---|---|---|---|
| a) ECD1-3 | | | | | |
| Round 1 | 40 µl/ml | $8*10^{11}$ | $2*10^6$ | $2.5*10^{-6}$ | |
| Round 2 | 40 µl/ml | $5*10^{10}$ | $2*10^5$ | $4*10^{-6}$ | 1.6 |
| Round 3 | 20 µl/ml | $5*10^{11}$ | $4*10^6$ | $10^{-5}$ | 2.5 |
| Round 4 | 20 µl/ml | $2*10^{11}$ | $5*10^8$ | $2.5*10^{-3}$ | 250 |
| b) ECD4 | | | | | |
| Round 1 | 40 µl/ml | $8*10^{11}$ | $2*10^7$ | $1.25*10^{-5}$ | |
| Round 2 | 40 µl/ml | $5*10^{10}$ | $10^5$ | $2*10^{-6}$ | 0.2 |
| Round 3 | 20 µl/ml | $5*10^{11}$ | $5*10^4$ | $10^{-7}$ | 0.05 |
| Round 4 | 20 µl/ml | $3.5*10^{11}$ | $5*10^5$ | $1.4*10^{-6}$ | 1.4 |

Screening 95 clones were isolated from the forth round of selection for ECD1-3 and ECD4 and tested by ELISA. The 95 clones isolated from the forth round of selection for ECD1-3-6HIS were screened against ECD1-3-6HIS and ECD1-3-GST. 93 out of 95 clones were positive when tested on ECD1-3-6HIS. Twenty two of the clones positive for ECD1-3-6HIS were also positive of for ECD1-3-GST. The twenty two clones positive both for ECD1-3-6HIS and ECD1-3-GST were finger printed to isolate unique clones. 7 clones had only one copy A7, C7, C12, D10, E4, E10 and G2. B12 had one other copy. D4 had 3 other copies and A8 had 8 other copies. A8 NcoI-NotI insert was shorter that the other clones when analyzed on an agarose gel. The 95 clones isolated from the forth round of selection for ECD4-6HIS were screened against and ECD4-6HIS and ECD1-3 6HIS. All the 95 clones tested were positive when tested on ECD4-6HIS and negative when tested on ECD1-3-6HIS. We selected 8 of the positive clones that gave the stronger signal on ELISA and fingerprinted them. These 8 clones had the same fingerprint. One of these clones, A1 was renamed A14.

In summary, we selected 10 individual phage clones that bind N-cadherin ECD1-3 recombinant protein (A7, A8, B12, C7, C12, D4, D10, E4, E 10, G2) and one phage clone that binds N-cadherin ECD4 recombinant protein (A14) .

Binding of Phage Clones to Cell Surface N-Cadherin

The eleven individual phage clones selected by ELISA were tested for cell binding of N-cadherin positive cells (PC3 and LNCaP N-cadherin transfected cells) by flow cytometry. Clones were also tested for cross-reactivity on N-cadherin negative cells (DU-145 and LNCap). For these experiments, a second batch of phage antibodies were generated and retested by ELISA. Both ELISA results for the selected clones are presented in Table 2. All phage clones except one D4 stained N-cadherin positive cells but not N-cadherin negative cells. The mean fluorescence intensity for each clone is presented in Table 2. We selected A14 as the only anti-ECD4 and the C7 and E4 as these phage antibody clones show the strongest cell staining to be reformatted into diabody. The diabody generated; A14Db, C7Db and E4 Db were used to stain N-cadherin positive and negative cells. A14Db and E4Db showed a comparable weak staining while C7 Db showed stronger staining of N-cadherin positive cells when analyzed by flow cytometry(data not shown). However C7Db also show staining of an N-cadherin negative cell.

scFv protein from these clones have been sequenced. The sequences are listed below:

| | |
|---|---|
| A14 ScFv | SEQ ID NO: 1 |
| A7 Incomplete ScFv | SEQ ID NO: 2 |
| A8 Truncated ScFv | SEQ ID NO: 3 |
| B12 Incomplete ScFv | SEQ ID NO: 4 |
| C7 ScFc | SEQ ID NO: 5 |
| C12 Incomplete ScFv | SEQ ID NO: 6 |
| D4 ScFv | SEQ ID NO: 7 |
| E4 ScFv | SEQ ID NO: 8 |
| E10 Incomplete ScFv | SEQ ID NO: 9 |

TABLE 2

| Clone | Fusion protein | Number of copies | 1$^{St}$ ELISA (O.D) | 2$^{nd}$ ELISA (O.D) | Flow Cytometry (MFI) |
|---|---|---|---|---|---|
| A14 (A1) | HIS Domain 4 | 1 | 0.32 | ? | 57 |
| A7 | GST | 1 | 0.1 | 0 | 48 |
|  | HIS |  | 0.26 | 0.38 |  |
| A8 (truncated) | GST | 9 | 0.17 | 0.05 | 30 |
|  | HIS |  | 0.25 | 0.11 |  |
| B12 | GST | 2 | 0.2 | 0.26 | 91 |
|  | HIS |  | 0.18 | 0.4 |  |
| C7 | GST | 1 | 0.1 | 0.19 | 110 |
|  | HIS |  | 0.23 | 0.35 |  |
| C12 | GST | 1 | 0.34 | 0.16 | 38 |
|  | HIS |  | 0.2 | 0.31 |  |
| D4 | GST | 4 | 0.31 | 0.15 | 0 |
|  | HIS |  | 0.38 | 0.24 |  |
| D10 | GST | 1 | 0.22 | 0.13 | 25 |
|  | HIS |  | 0.24 | 0.28 |  |
| E4 | GST | 1 | 0.17 | 0.21 | 216 |
|  | HIS |  | 0.35 | 0.39 |  |
| E10 | GST | 1 | 0.13 | 0.14 | 12 |
|  | HIS |  | 0.21 | 0.35 |  |
| G2 | GST | 1 | 0.09 | 0.06 | 36 |
|  | HIS |  | 0.26 | 0.14 |  |

TABLE 3

| | Tumor | Blood | Liver | Spleen | Kidney | Lung |
|---|---|---|---|---|---|---|
| LAPC9 AI | 0.6 | 0.9 | 0.3 | 0.2 | 0.6 | 0.3 |
| PC3 | 0.3 | 0.6 | 0.3 | 0.1 | 0.6 | 0.3 |

Biodistribution data obtained 22 h post injection of tumors or mice.

Tumor/blood=0.7 (LAPC9) and 0.5 (PC3)

Selection of the Best Binder.

In an additional effort to select the best out of the 10 ECD1-3 binders, these phage clones were generated, depleted on LNCaP cells and panned twice against N-cadherin transfected LNCaP cells. Clones were sequenced. Although, staining of N-cadherin transfected LNCaP cells with D4 phage clones were negative, D4 clone was prevalent with X copies.

Figure 2:
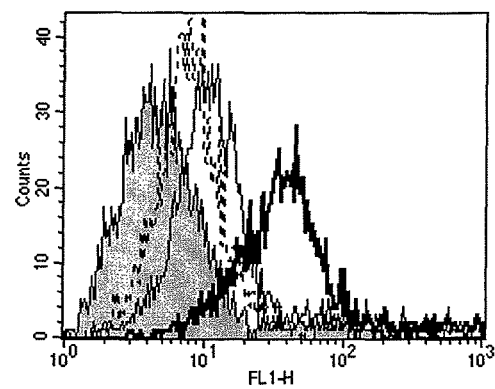
FIG. 2. A14, C7, E4 and D4 diabody staining of PC3 cells.

D4 diabody (D4Db) was generated and compared to E4Db for PC3 and DU145 staining (FIG. 2). Both E4Db and D4Db stained PC3 and were negative for DU145. D4Db staining of PC3 was stronger than E4Db (FIG. 4).

As shown in FIG. 2, N-cadherin positive cells (PC3) were incubated with diabodies, stained and analyzed by flow cytometry. Secondary antibodies only: anti-C-Myc-FITC (filled in gray), A14 Db (dashed line), E4 Db (thin line) C7 Db (thick line).

Figure 3:
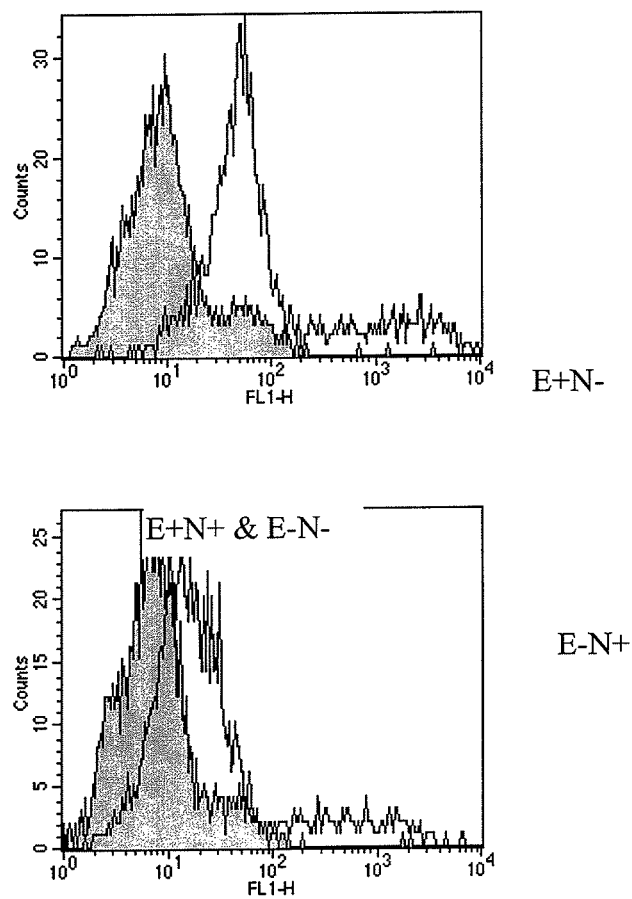
FIG. 3. Binding of C7 diabody to N-cadherin negative cells.

As shown in FIG. 3, N-cadherin negative cells (DU 145) and N-cadherin positive cells (PC3) were incubated with C7 Db, stained and analyzed by flow cytometry. Secondary antibodies only: anti-C-Myc-FITC (filled in gray), C7 Db (solid line).

Figure 4:
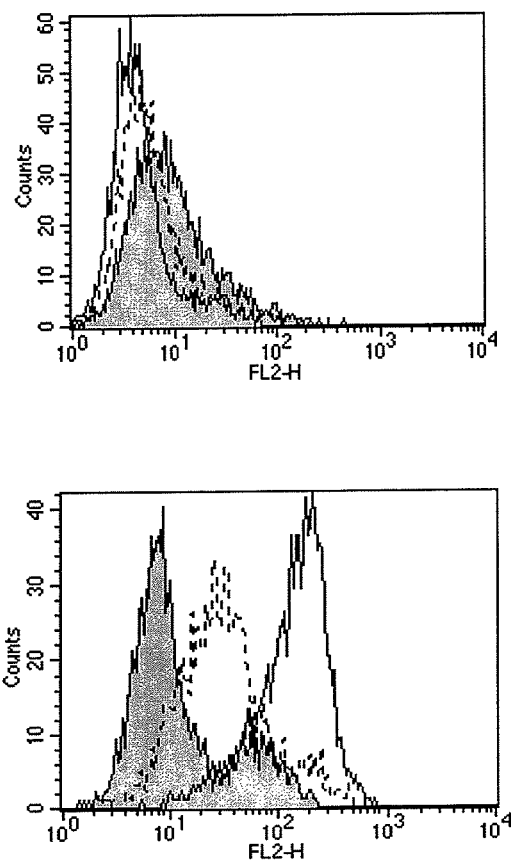
FIG. 4. Specific binding of E4 and D4 diabodies to N-cadherin expressing cells.

As shown in FIG. 4, N-cadherin negative cells (DU 145) and N-cadherin positive cells (PC3) were incubated with diabodies, stained and analyzed by flow cytometry. Secondary antibodies only: anti-C-Myc-biotin an spteptavidin R-PE (filled in gray), E4 Db (dashed line), D4 Db (solid line).

Figure 5:
FIG. 5. Tumor localization of $^{124}$I labeled D4 Db in LAPC9 Al tumors.
Figure 6:
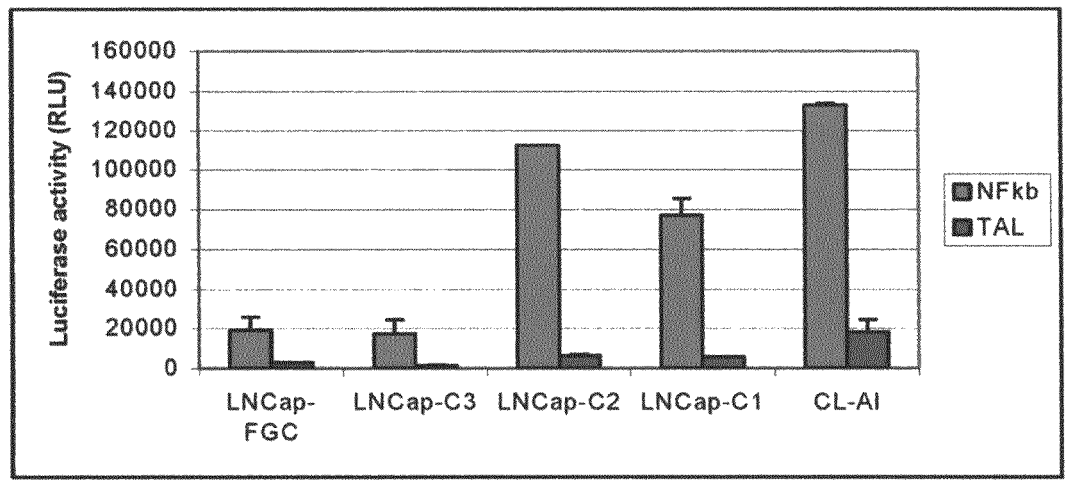
FIG. 6. N-cadherin Activates NF-κB.

FIG. 5 shows the tumor localization of $^{124}$I labeled D4 Db in LAPC9 AI tumors. Coronal section registered 4h hours post injection.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A monoclonal antibody or fragment thereof comprising the amino acid sequence of SEQ ID NO:1, wherein the antibody or fragment thereof is capable of binding to extracellular domain 4 of N-cadherin.

2. The antibody of claim 1, wherein the fragment is a scFv.

3. The antibody of claim 1, wherein the fragment is a diabody.

* * * * *

UNITED STATES PATENT AND TRADEMARK OFFICE
CERTIFICATE OF CORRECTION

| | | |
|---|---|---|
| PATENT NO. | : 8,703,920 B2 | Page 1 of 1 |
| APPLICATION NO. | : 12/590601 | |
| DATED | : April 22, 2014 | |
| INVENTOR(S) | : Robert E. Reiter, Eric Lepin and Anna M. Wu | |

It is certified that error appears in the above-identified patent and that said Letters Patent is hereby corrected as shown below:

In the Specification

Column 1, please delete the entire paragraph beginning at lines 11 through 18 and replace it with the following paragraph:

-- This invention was made with Government support under Grant No. CA092131 and CA098010, awarded by the National Institutes of Health. The Government has certain rights in the invention. --

Signed and Sealed this
Second Day of September, 2014

Michelle K. Lee
*Deputy Director of the United States Patent and Trademark Office*

SEQUENCE LISTING

```
<160> NUMBER OF SEQ ID NOS: 12

<210> SEQ ID NO 1
<211> LENGTH: 246
<212> TYPE: PRT
<213> ORGANISM: Artificial Sequence
<220> FEATURE:
<223> OTHER INFORMATION: synthetic A14 scFv

<400> SEQUENCE: 1

Met Ala Gln Val Gln Leu Val Gln Ser Gly Gly Gly Leu Ala Gln Pro
1               5                   10                  15

Gly Gly Ser Leu Arg Leu Ser Cys Ala Ala Ser Gly Phe Thr Phe Ser
            20                  25                  30

Arg His Ala Met Ile Trp Val Arg Gln Ala Pro Gly Lys Gly Leu Glu
        35                  40                  45

Trp Val Ser Ser Ile Ser Gly Ser Ser Asp Ser Thr Ser Tyr Ala Asp
    50                  55                  60
```

Ser Val Lys Gly Arg Phe Thr Ile Ser Arg Asp Asn Ser Lys Asn Thr
65                  70                  75                  80

Leu Tyr Leu Gln Met Asn Thr Leu Arg Ala Glu Asp Thr Ala Val Tyr
            85                  90                  95

Tyr Cys Ala Lys Ala Thr Gly Tyr Ser Tyr Tyr Gly Met Asp Val
            100                 105                 110

Trp Gly Pro Gly Thr Thr Val Thr Val Ser Ser Gly Gly Gly Ser
            115                 120                 125

Gly Gly Gly Gly Ser Gly Gly Gly Ser Asp Ile Gln Met Thr Gln
            130                 135                 140

Ser Pro Ser Ser Leu Ser Ala Ser Leu Gly Asp Arg Val Thr Ile Thr
145                 150                 155                 160

Cys Arg Ala Ser Gln Gly Ile Ser Asn Tyr Leu Ala Trp Tyr Gln Gln
                165                 170                 175

Lys Pro Gly Lys Ala Pro Lys Leu Leu Ile Tyr Gly Ala Thr Thr Leu
            180                 185                 190

Gln His Gly Val Pro Ser Arg Phe Ser Gly Ser Gly Ser Gly Thr Asp
            195                 200                 205

Phe Ser Leu Thr Ile Ser Ser Leu Gln Pro Glu Asp Phe Ala Ile Tyr
210                 215                 220

Phe Cys Gln Gln Ala His Ser Phe Pro Pro Thr Phe Gly Gly Gly Thr
225                 230                 235                 240

Lys Leu Glu Ile Lys Arg
            245

<210> SEQ ID NO 2
<211> LENGTH: 89
<212> TYPE: PRT
<213> ORGANISM: Artificial Sequence
<220> FEATURE:
<223> OTHER INFORMATION: synthetic A7 incomplete scFv

<400> SEQUENCE: 2

Met Ala Gln Val Gln Leu Val Gln Ser Gly Ala Glu Val Lys Lys Pro
1               5                   10                  15

Gly Ala Ser Val Lys Val Ser Cys Gln Ala Ser Gly Tyr Thr Phe Thr
            20                  25                  30

Ser Tyr Tyr Ile His Trp Val Arg Gln Ala Pro Gly Gln Gly Phe Glu
            35                  40                  45

Trp Met Gly Ile Ile Asn Pro Ser Gly Gly Ser Ala Ser Tyr Ala Gln
    50                  55                  60

Lys Phe Gln Gly Arg Val Thr Met Thr Arg Asp Thr Ser Thr Ser Thr
65                  70                  75                  80

Val Tyr Met Glu Leu Arg Ser Leu Arg
                85

<210> SEQ ID NO 3
<211> LENGTH: 148
<212> TYPE: PRT
<213> ORGANISM: Artificial Sequence
<220> FEATURE:
<223> OTHER INFORMATION: synthetic A8 truncated scFv

<400> SEQUENCE: 3

Met Ala Gln Val Gln Leu Gln Glu Ser Gly Trp Tyr Phe Asp Leu Trp
1               5                   10                  15

Gly Arg Gly Thr Pro Val Thr Val Ser Ser Gly Gly Gly Gly Ser Gly
            20                  25                  30

-continued

Gly Gly Gly Ser Gly Gly Gly Ser Glu Ile Val Leu Thr Gln Ser
            35                  40                  45

Pro Ser Ser Leu Ser Ala Ser Val Gly Asp Arg Val Thr Ile Thr Cys
 50                  55                  60

Arg Ala Ser Gln Gly Ile Arg Asn Asp Leu Gly Trp Tyr Gln Gln Lys
 65                  70                  75                  80

Pro Gly Lys Ala Pro Lys Leu Leu Ile Tyr Ala Ala Ser Ser Leu Gln
                 85                  90                  95

Ser Gly Val Pro Ser Arg Phe Ser Gly Ser Gly Ser Gly Thr Asp Phe
            100                 105                 110

Thr Leu Thr Ile Ser Ser Leu Gln Pro Glu Asp Phe Ala Thr Tyr Tyr
        115                 120                 125

Cys Leu Gln Asp Tyr Asn Gly Trp Thr Phe Gly Gln Gly Thr Lys Val
    130                 135                 140

Glu Ile Lys Arg
145

<210> SEQ ID NO 4
<211> LENGTH: 209
<212> TYPE: PRT
<213> ORGANISM: Artificial Sequence
<220> FEATURE:
<223> OTHER INFORMATION: synthetic B12 incomplete scFv

<400> SEQUENCE: 4

Met Ala Gln Val Gln Leu Val Glu Ser Gly Gly Gly Val Val Gln Pro
  1               5                  10                  15

Gly Arg Ser Leu Arg Leu Ser Cys Ala Ala Ser Gly Phe Ser Phe Ser
             20                  25                  30

Asn Tyr Gly Met His Trp Val Arg Gln Ala Pro Gly Lys Gly Leu Glu
         35                  40                  45

Trp Val Ala Val Ile Ser Tyr Asp Gly Arg Val Lys Ser Tyr Ala Asp
     50                  55                  60

Ala Val Lys Gly Arg Phe Thr Ile Ser Arg Asp Asn Ser Glu Asn Ile
 65                  70                  75                  80

Leu Tyr Val Gln Ile Asp Ser Leu Arg Val Glu Asp Thr Ala Val Tyr
                 85                  90                  95

Tyr Cys Ala Arg Arg Gly Gly Asp His Ala Ala Gly Met Asp Val Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Ser Gln Ser Ala Leu Thr Gln Pro
    130                 135                 140

Ala Ser Val Ser Gly Ser Pro Gly Gln Ser Ile Thr Ile Ser Cys Thr
145                 150                 155                 160

Gly Gly Arg Ser Asp Ile Gly Gly Tyr Asn Tyr Val Ser Trp Tyr Gln
                165                 170                 175

Gln His Pro Gly Lys Ala Pro Lys Leu Met Ile Tyr Asp Val Gly Asn
            180                 185                 190

Arg Pro Ser Gly Val Ser Asn Arg Phe Ser Gly Ser Lys Ser Gly Asn
        195                 200                 205

Thr

<210> SEQ ID NO 5
<211> LENGTH: 246
<212> TYPE: PRT

<213> ORGANISM: Artificial Sequence
<220> FEATURE:
<223> OTHER INFORMATION: synthetic C7 scFv
<221> NAME/KEY: VARIANT
<222> LOCATION: (94)...(94)
<223> OTHER INFORMATION: Xaa = any amino acid

<400> SEQUENCE: 5

```
Met Ala Pro Gly Ala Gly Gly Val Gly Gly Val Val Gln Pro
1               5                   10                  15

Gly Arg Ser Leu Arg Leu Ser Cys Ala Ala Ser Gly Phe Thr Phe Ser
            20                  25                  30

Ser Tyr Gly Met His Trp Val Arg Gln Ala Pro Gly Lys Gly Leu Glu
        35                  40                  45

Trp Val Ala Val Ile Ser Tyr Asp Gly Ser Asn Lys Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Xaa Val Tyr
                85                  90                  95

Tyr Cys Ala Arg Leu Glu Tyr Ser Ser Ser Arg Ala Phe Asp Val
            100                 105                 110

Trp Gly Gln Gly Thr Thr Val Thr Val Ser Ser Gly Gly Gly Ser
            115                 120                 125

Gly Gly Gly Gly Ser Gly Gly Gly Ser Ser Glu Leu Thr Gln Asp
            130                 135                 140

Pro Ala Val Ser Val Ala Leu Gly Gln Thr Val Arg Ile Thr Cys Gln
145                 150                 155                 160

Gly Asp Ser Leu Arg Ser Tyr Tyr Ala Ser Trp Tyr Gln Gln Lys Pro
                165                 170                 175

Gly Gln Ala Pro Val Leu Val Ile Tyr Gly Lys Asn Asn Arg Pro Ser
            180                 185                 190

Gly Ile Pro Asp Arg Phe Ser Gly Ser Ser Ser Gly Asn Thr Ala Ser
            195                 200                 205

Leu Thr Ile Thr Gly Ala Gln Ala Glu Asp Glu Ala Asp Tyr Tyr Cys
    210                 215                 220

Asn Ser Arg Asp Ser Ser Gly Asn His Val Val Phe Gly Gly Gly Thr
225                 230                 235                 240

Lys Leu Thr Val Leu Gly
                245
```

<210> SEQ ID NO 6
<211> LENGTH: 29
<212> TYPE: PRT
<213> ORGANISM: Artificial Sequence
<220> FEATURE:
<223> OTHER INFORMATION: synthetic C12 incomplete scFv

<400> SEQUENCE: 6

```
Met Ala Gln Val Gln Leu Val Glu Ser Gly Gly Gly Val Val Gln Pro
1               5                   10                  15

Gly Arg Ser Leu Arg Leu Ser Cys Ala Ala Ser Gly Phe
            20                  25
```

<210> SEQ ID NO 7
<211> LENGTH: 245
<212> TYPE: PRT
<213> ORGANISM: Artificial Sequence
<220> FEATURE:
<223> OTHER INFORMATION: synthetic D4 scFv

<400> SEQUENCE: 7

```
Met Ala Gln Val Gln Leu Val Gln Ser Gly Ala Glu Val Lys Arg Pro
 1               5                   10                  15

Gly Ala Ser Val Arg Ile Ser Cys Lys Ala Ser Gly Tyr Pro Phe Thr
            20                  25                  30

Thr Tyr Pro Ile His Trp Val Arg Gln Ala Pro Gly Gln Gly Leu Glu
        35                  40                  45

Trp Met Gly Gly Ile Asn Pro Asn Ser Gly Ala Thr Lys Asn Val Gln
50                  55                  60

Lys Phe Gln Gly Arg Val Thr Met Thr Ala Asp Thr Ser Ile Arg Thr
65                  70                  75                  80

Ala Tyr Met Glu Leu Ser Arg Leu Thr Ser Asp Asp Thr Ala Val Tyr
                85                  90                  95

Tyr Cys Ala Arg Gly Glu Gly Asp Thr Gly Ser Tyr Leu Gly Gly Tyr
            100                 105                 110

Trp Gly Leu Gly Thr Leu Val Thr Val Ser Ser Gly Gly Gly Gly Ser
        115                 120                 125

Gly Gly Gly Gly Ser Gly Gly Gly Ser Ser Glu Leu Thr Gln Asp
130                 135                 140

Pro Ala Val Ser Val Ala Leu Gly Gln Thr Val Arg Ile Thr Cys Gln
145                 150                 155                 160

Gly Asp Ser Leu Arg Ser Tyr Tyr Ala Ser Trp Tyr Gln Gln Lys Pro
                165                 170                 175

Gly Arg Ala Pro Leu Leu Val Ile Tyr Gly Lys Asn Ile Arg Pro Ser
            180                 185                 190

Gly Ile Pro Asp Arg Phe Ser Gly Ser Ser Ser Gly Asn Ser Ala Ser
        195                 200                 205

Leu Thr Ile Thr Gly Ala Gln Ala Glu Asp Glu Ala Asp Tyr Tyr Cys
    210                 215                 220

Asn Ser Arg Asp Arg Ser Gly Asn Tyr Leu Phe Gly Val Gly Thr Lys
225                 230                 235                 240

Val Thr Val Leu Gly
                245
```

<210> SEQ ID NO 8
<211> LENGTH: 247
<212> TYPE: PRT
<213> ORGANISM: Artificial Sequence
<220> FEATURE:
<223> OTHER INFORMATION: synthetic E4 scFv

<400> SEQUENCE: 8

```
Met Ala Gln Val Gln Leu Val Gln Ser Gly Ala Glu Val Lys Lys Pro
 1               5                   10                  15

Gly Glu Ser Leu Glu Ile Ser Cys Lys Gly Ser Gly Tyr Ser Phe Ala
            20                  25                  30

Asn Asn Trp Ile Gly Trp Val Arg Gln Met Pro Gly Lys Gly Leu Glu
        35                  40                  45

Trp Met Gly Ser Ile Tyr Pro Gly Asp Ser Asp Val Arg Tyr Ser Arg
50                  55                  60

Ser Phe Gln Gly His Val Thr Ile Ser Ala Asp Lys Ser Ile Ser Thr
65                  70                  75                  80

Ala Tyr Leu Gln Trp Ser Ser Leu Lys Ala Ser Asp Thr Ala Met Tyr
                85                  90                  95

Tyr Cys Ala Arg His Arg Val Ala Tyr Ser Gly Tyr Asp Ala Phe Asp
```

```
            100                 105                 110
Ile Trp Gly Gln Gly Thr Met Val Thr Val Ser Ser Gly Gly Gly
        115                 120                 125

Ser Gly Gly Gly Gly Ser Gly Gly Gly Ser Ser Val Leu Thr Gln
        130                 135                 140

Asp Pro Ala Val Ser Val Ala Leu Gly Gln Thr Val Arg Ile Thr Cys
145                 150                 155                 160

Gln Gly Asp Ser Leu Arg Ser Tyr Tyr Pro Ser Trp Tyr Gln Gln Lys
                    165                 170                 175

Pro Gly Gln Ala Pro Val Leu Val Ile Tyr Gly Lys Asn Asn Arg Pro
                180                 185                 190

Ser Gly Ile Pro Asp Arg Phe Ser Gly Ser Ser Ser Gly Asn Thr Ala
            195                 200                 205

Ser Leu Thr Ile Thr Gly Ala Gln Ala Glu Asp Glu Ala Asp Tyr Tyr
210                 215                 220

Cys His Ser Arg Asp Arg Ser Gly Asn Gln Val Leu Phe Gly Gly
225                 230                 235                 240

Thr Lys Val Thr Val Leu Gly
                245

<210> SEQ ID NO 9
<211> LENGTH: 147
<212> TYPE: PRT
<213> ORGANISM: Artificial Sequence
<220> FEATURE:
<223> OTHER INFORMATION: synthetic E10 incomplete scFv

<400> SEQUENCE: 9

Met Ala Gln Val Gln Leu Val Gln Ser Gly Gly Gly Val Val Gln Pro
  1                   5                  10                  15

Gly Arg Ser Leu Arg Leu Ser Cys Ala Ala Ser Gly Phe Thr Phe Ser
                 20                  25                  30

Ser Tyr Gly Met His Trp Val Arg Gln Ala Pro Gly Lys Gly Leu Glu
             35                  40                  45

Trp Val Ala Val Ile Trp Tyr Asp Gly Ser Asn Lys Tyr Tyr Ala Asp
 50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                 85                  90                  95

Tyr Cys Ala Arg Val Gly Gly Glu Gly Val Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Ser Thr Leu
    130                 135                 140

Ser Ala Ser
145

<210> SEQ ID NO 10
<211> LENGTH: 16
<212> TYPE: PRT
<213> ORGANISM: Artificial Sequence
<220> FEATURE:
<223> OTHER INFORMATION: synthetic scFv linker

<400> SEQUENCE: 10

Ser Gly Gly Gly Gly Ser Gly Gly Gly Gly Ser Gly Gly Gly Gly Ser
```

-continued

```
             1               5              10              15

<210> SEQ ID NO 11
<211> LENGTH: 6
<212> TYPE: PRT
<213> ORGANISM: Artificial Sequence
<220> FEATURE:
<223> OTHER INFORMATION: synthetic diabody linker

<400> SEQUENCE: 11

Ser Gly Gly Gly Gly Ser
  1               5

<210> SEQ ID NO 12
<211> LENGTH: 6
<212> TYPE: PRT
<213> ORGANISM: Artificial Sequence
<220> FEATURE:
<223> OTHER INFORMATION: synthetic 6 histidine tag, 6HIS tag

<400> SEQUENCE: 12

His His His His His His
  1               5
```